US011635390B2

(12) United States Patent
Nakayama et al.

(10) Patent No.: US 11,635,390 B2
(45) Date of Patent: *Apr. 25, 2023

(54) MEASUREMENT CYCLE DETERMINATION DEVICE, MEASUREMENT CYCLE DETERMINATION PROGRAM AND METHOD THEREOF

(71) Applicant: 3M INNOVATIVE PROPERTIES COMPANY, St. Paul, MN (US)

(72) Inventors: Tasuku Nakayama, Ninomiya (JP); Kazuma Nuno, Sagamihara (JP)

(73) Assignee: 3M Innovative Properties Company, St. Paul, MN (US)

(*) Notice: Subject to any disclaimer, the term of this patent is extended or adjusted under 35 U.S.C. 154(b) by 4 days.

This patent is subject to a terminal disclaimer.

(21) Appl. No.: 17/173,392

(22) Filed: Feb. 11, 2021

(65) Prior Publication Data

US 2021/0164911 A1 Jun. 3, 2021

Related U.S. Application Data

(63) Continuation of application No. 16/461,051, filed as application No. PCT/US2017/060798 on Nov. 9, 2017, now Pat. No. 10,955,356.

(30) Foreign Application Priority Data

Nov. 17, 2016 (JP) ................................. 2016-224222

(51) Int. Cl.
*G01N 21/88* (2006.01)
*G01N 33/38* (2006.01)
*G06Q 10/06* (2023.01)

(52) U.S. Cl.
CPC ..... *G01N 21/8851* (2013.01); *G01N 21/8803* (2013.01); *G01N 21/8806* (2013.01);
(Continued)

(58) Field of Classification Search
CPC ....... G01N 2021/8845; G01N 21/8803; G01N 21/8806; G01N 21/8851; G01N 33/383; G06Q 10/06
See application file for complete search history.

(56) References Cited

U.S. PATENT DOCUMENTS

| 7,840,376 | B2 | 11/2010 | Torng |
| 10,955,356 | B2* | 3/2021 | Nakayama ............. G06Q 10/06 |
| 2009/0240468 | A1 | 9/2009 | Torng |
| 2015/0127467 | A1 | 5/2015 | Hoyle |

FOREIGN PATENT DOCUMENTS

| JP | 4107359 | 4/1992 |
| JP | H10301986 | 11/1998 |

(Continued)

OTHER PUBLICATIONS

Weather news, [retrieved from the internet on Jul. 5, 2019], URL <http://weathernews.jp/>, 1page.

(Continued)

*Primary Examiner* — Peter B Kim
(74) *Attorney, Agent, or Firm* — Sriram Srinivasan

(57) ABSTRACT

To suitably determine a measurement cycle at which to measure cracks that occur in structures formed from concrete or the like.
Resolution Means:
A measurement cycle determination device (2) includes a related information acquisition unit (41) that acquires at least one of geographic information including items related to a geography of a site where a structure is located, weather information including items related to weather at the site, and structure information including items related to the structure; a crack information acquisition unit (42) that acquires crack information related to a crack that has occurred in the structure; a measurement cycle determination unit (44) that determines, on the basis of at least one of the geographic information, the weather information, the (Continued)

structure information, and the crack information, a measurement cycle at which to measure a width of the crack; and a measurement cycle output unit (46) that outputs a measurement cycle signal indicating measurement cycle information related to the determined measurement cycle.

10 Claims, 32 Drawing Sheets

(52) U.S. Cl.
CPC ........... *G01N 33/383* (2013.01); *G06Q 10/06* (2013.01); *G01N 2021/8845* (2013.01)

(56) References Cited

FOREIGN PATENT DOCUMENTS

| | | |
|---|---|---|
| JP | 2003-118794 | 4/2003 |
| JP | 2005-018116 | 1/2005 |
| JP | 2006-251914 | 9/2006 |
| JP | 2007-140608 | 6/2007 |
| JP | 2007-178292 | 7/2007 |
| JP | 2007178292 A | 7/2007 |
| JP | 2010128717 | 6/2010 |
| JP | 2011-191282 | 9/2011 |
| JP | 2011191282 A | 9/2011 |
| JP | 2012-103960 | 5/2012 |
| JP | 2012103960 A | 5/2012 |
| JP | 2012-247229 | 12/2012 |
| JP | 2015183136 | 10/2015 |
| JP | 2016-004285 | 1/2016 |
| WO | WO 2015-142779 | 9/2015 |
| WO | WO 2017-048610 | 3/2017 |

OTHER PUBLICATIONS

Yahoo Answers, [retrieved from the internet on Jul. 5, 2019], URL <https://answers.yahoo.com/>, 2pages.
International Search report for PCT International Application No. PCT/US2017/060798 dated Jan. 8, 2018, 4 pages.

* cited by examiner

↑ SECOND DIRECTION   ↑ FIRST DIRECTION
←——— THIRD DIRECTION

↑ SECOND DIRECTION   ↑ FIRST DIRECTION
←——— THIRD DIRECTION

SITE INFORMATION

DRAWING INFORMATION

SITE ID: 0001
SITE POSITION INFORMATION:
E139, N35
CONSTRUCTION YEAR: 1972
STRUCTURE TYPE: BRIDGE
MATERIAL: REINFORCED CONCRETE
GROUND STRENGTH: OK
RECORD HIGHEST TEMPERATURE: 38°C
RECORD LOWEST TEMPERATURE: -9°C
RECORD HIGHEST SNOW
ACCUMULATION: 43 mm/h
HIGHEST SEISMIC INTENSITY
IN PAST 10 YEARS: 4
STRUCTURE NAME: BRIDGE ABC

⋮

DRAWING ID: 0001
SITE ID: 0001

FIG. 13

SITE INFORMATION

SITE ID: 0001
SITE POSITION INFORMATION:
E139, N35
CONSTRUCTION YEAR: 1972
STRUCTURE TYPE: BRIDGE
MATERIAL: REINFORCED CONCRETE
GROUND STRENGTH: OK
RECORD HIGHEST TEMPERATURE: 38°C
RECORD LOWEST TEMPERATURE: -9°C
RECORD HIGHEST SNOW
ACCUMULATION: 43 mm/h
HIGHEST SEISMIC INTENSITY
IN PAST 10 YEARS: 4
STRUCTURE NAME: BRIDGE ABC

•
•
•

DRAWING INFORMATION

DRAWING ID: 0001
SITE ID: 0001

SHEET INFORMATION

SHEET ID: 0001
SITE ID: 0001
DRAWING ID: 0001
SHEET POSITION NAME: NORTH PIER 2
SHEET AFFIXED COORDINATES: 32, 100
PRINTING PATTERN:
PARALLEL STRAIGHT LINES
PITCH WIDTH: 0.5 mm
OFFSET ANGLE: 3°
INITIAL CRACK WIDTH: 0.1 mm

| ITEM | SUB-ITEM | +1 POINT CONDITIONS | +2 POINTS CONDITIONS |
|---|---|---|---|
| GEOGRAPHIC INFORMATION | GROUND STRENGTH | WEAK | |
| | SALT DAMAGE | YES | |
| | HIGHEST SEISMIC INTENSITY | SEISMIC INTENSITY OF 4 OR HIGHER IN PAST 10 YEARS | SEISMIC INTENSITY OF 5 OR HIGHER IN PAST 10 YEARS |
| | FREQUENCY OF EARTHQUAKES | ONE OR MORE WITH SEISMIC INTENSITY OF 1 OR HIGHER PER MONTH | TWO OR MORE WITH SEISMIC INTENSITY OF 1 OR HIGHER PER MONTH |
| | ... | | |
| WEATHER INFORMATION | HIGHEST TEMPERATURE | 30°C OR HIGHER | |
| | LOWEST TEMPERATURE | -10°C OR LOWER | |
| | HIGHEST HUMIDITY | 90% OR HIGHER | |
| | LOWEST HUMIDITY | 10% OR LOWER | |
| | MAXIMUM WIND SPEED | 30 m/s OR FASTER | |
| | MAXIMUM RAINFALL | 100 mm OR MORE IN ONE HOUR | |
| | MAXIMUM SNOWFALL | 20 mm OR MORE IN ONE HOUR | |
| | ... | | |
| STRUCTURE INFORMATION | CONSTRUCTION YEAR | 1990 OR EARLIER | 1980 OR EARLIER |
| | MATERIAL | OTHER THAN REINFORCED CONCRETE | |
| | TYPE | BRIDGE, TUNNEL | |
| | SECTION | PIER, BRIDGE GIRDER, TUNNEL INNER WALL | |
| | ... | | |
| CRACK INFORMATION | INITIAL CRACK WIDTH | 1 mm | |
| | GROWTH RATE FROM INITIAL CRACK WIDTH | 10% | |
| | GROWTH RATE FROM PREVIOUS CRACK WIDTH | 30% | |
| | ... | | |

FIG. 18

SITE INFORMATION

SITE ID: 0001
SITE POSITION INFORMATION:
E139, N35
CONSTRUCTION YEAR: 1972
STRUCTURE TYPE: BRIDGE
MATERIAL: REINFORCED CONCRETE
GROUND STRENGTH: OK
RECORD HIGHEST TEMPERATURE: 38°C
RECORD LOWEST TEMPERATURE: -9°C
RECORD HIGHEST SNOW
ACCUMULATION: 43 mm/h
HIGHEST SEISMIC INTENSITY
IN PAST 10 YEARS: 4
STRUCTURE NAME: BRIDGE ABC

⋮

DRAWING INFORMATION

DRAWING ID: 0001
SITE ID: 0001

SHEET INFORMATION

SHEET ID: 0001
SITE ID: 0001
DRAWING ID: 0001
SHEET POSITION NAME: NORTH PIER 2
SHEET AFFIXED COORDINATES: 32, 100
PRINTING PATTERN:
PARALLEL STRAIGHT LINES
PITCH WIDTH: 0.5 mm
OFFSET ANGLE: 3°
INITIAL CRACK WIDTH: 0.1 mm
MEASUREMENT CYCLE: 12-MONTHS

⋮

MEASUREMENT INFORMATION

MEASUREMENT ID: 0001
SHEET ID: 0001
MEASUREMENT DATE: 2016/8/16
SHEET IMAGE STORAGE ADDRESS:
ADDRESS NO. XXXXX
ESTIMATED CRACK GROWTH WIDTH:
0 mm

SITE INFORMATION

SITE ID: 0001
SITE POSITION INFORMATION:
E139, N35
CONSTRUCTION YEAR: 1972
STRUCTURE TYPE: BRIDGE
MATERIAL: REINFORCED CONCRETE
GROUND STRENGTH: OK
RECORD HIGHEST TEMPERATURE: 38°C
RECORD LOWEST TEMPERATURE: -9°C
RECORD HIGHEST SNOW
ACCUMULATION: 43 mm/h
HIGHEST SEISMIC INTENSITY
IN PAST 10 YEARS: 4
STRUCTURE NAME: BRIDGE ABC

⋮

DRAWING INFORMATION

DRAWING ID: 0001
SITE ID: 0001

SHEET INFORMATION

SHEET ID: 0001
SITE ID: 0001
DRAWING ID: 0001
SHEET POSITION NAME: NORTH PIER 2
SHEET AFFIXED COORDINATES: 32, 100
PRINTING PATTERN:
PARALLEL STRAIGHT LINES
PITCH WIDTH: 0.5 mm
OFFSET ANGLE: 3°
CRACK WIDTH: 0.11 mm
MEASUREMENT CYCLE: 12-MONTHS

⋮

MEASUREMENT INFORMATION

MEASUREMENT ID: 0002
SHEET ID: 0001
DATE: 2017/8/16
SHEET IMAGE STORAGE ADDRESS:
ADDRESS NO. XXXXX
ESTIMATED CRACK GROWTH WIDTH:
0.01 mm

MEASUREMENT CYCLE DETERMINATION DEVICE, MEASUREMENT CYCLE DETERMINATION PROGRAM AND METHOD THEREOF

TECHNICAL FIELD

The present disclosure relates to a measurement cycle determination device, a measurement cycle determination program, and a method thereof.

BACKGROUND

Various techniques are known for efficiently and reliably executing maintenance inspection work of various structures such as bridges, levees, and tunnels, and also of buildings that have various facilities such as air conditioning equipment and electrical equipment. For example, Patent Document 1 describes calculating an annual total load of a building as a whole from an inspection load and inspection cycle for one instance of maintenance inspection work per piece of equipment; and determining a number of inspectors necessary for the maintenance inspection work needed for the maintenance management of the building. Additionally, Patent Document 2 describes displaying guidance information, which indicates a position of a facility to be inspected, on a terminal device used by an inspector; and displaying an inspection checklist for the facility to be inspected on the terminal device used by the inspector when the inspector is close to the facility to be inspected. Moreover, Patent Document 3 describes notifying an administrator in real time of inspection results obtained by an inspector inspecting a facility on the basis of an inspection manual displayed on a communication terminal.

CITATION LIST

Patent Literature

Patent Document 1: Japanese Unexamined Patent Application Publication No. H10-301986A
Patent Document 2: Japanese Patent No. 4107359B
Patent Document 3: Japanese Unexamined Patent Application Publication No. 2010-128717A

SUMMARY

Problem to be Solved

However, a technique has not been proposed for suitably determining a measurement cycle at which to measure cracks that occur in structures formed from concrete or the like.

In light of the foregoing, an object of the present disclosure is to provide a measurement cycle determination device, a measurement cycle determination program, and a measurement cycle determination method whereby it is possible to suitably determine a measurement cycle at which to measure cracks that occur in structures formed from concrete or the like.

Means to Solve the Problem

A measurement cycle determination device according to an embodiment of the present disclosure includes a related information acquisition unit configured to acquire at least one of geographic information including items related to a geography of a site where a structure is located, weather information including items related to weather at the site, and structure information including items related to the structure; a crack information acquisition unit configured to acquire crack information related to a crack that has occurred in the structure; a measurement cycle determination unit configured to determine, on the basis of at least one of the geographic information, the weather information, the structure information, and the crack information, a measurement cycle at which to measure a width of the crack; and a measurement cycle output unit configured to output a measurement cycle signal indicating measurement cycle information related to the determined measurement cycle.

The measurement cycle determination device may further include a measurement cycle updating unit configured to update the measurement cycle on the basis of the crack information; wherein the measurement cycle output unit is configured to output an update measurement cycle signal indicating the updated measurement cycle.

With the measurement cycle determination device described above, a configuration is possible in which the crack information includes image data representing an image captured of a sheet affixed to the crack. In such a configuration, the sheet includes a first layer portion including a first pattern that includes a plurality of line drawings extending in a first direction, and a second layer portion including a second pattern that overlaps the first layer portion and that includes a plurality of line drawings extending in a second direction different than the first direction. Additionally, a moiré occurs in the sheet due to first pattern and the second pattern overlapping. Moreover, the measurement cycle updating unit includes a crack growth width estimation unit configured to estimate a growth width of the crack on the basis of a comparison of the moiré corresponding to the image data acquired previously and the moiré corresponding to the image acquired presently.

With the measurement cycle determination device described above, a configuration is possible in which the crack information includes at least one of the growth width of the crack and the width of the crack.

With the measurement cycle determination device described above, a configuration is possible in which at least one item included in the geographic information, the weather information, the structure information, and the crack information is associated with a numerical value; and the measurement cycle determination unit is configured to determine a predetermined first cycle for the measurement cycle when a total value of numerical values associated with a predetermined item is less than or equal to a predetermined first threshold value.

With the measurement cycle determination device described above, a configuration is possible in which the measurement cycle determination unit includes a quantification unit configured to quantify each item included in at least one of the geographic information, the weather information, the structure information, and the crack information as a numerical value representing a classification; a total value calculation unit configured to calculate the total value by adding the numerical values quantified by the quantification unit; and a first judgment unit configured to determine the first cycle for the measurement cycle when the total value is less than or equal to the first threshold value.

With the measurement cycle determination device described above, a configuration is possible in which the measurement cycle determination unit is configured to determine a cycle shorter than the first cycle for the measurement cycle when the total value is greater than the first threshold value.

With the measurement cycle determination device described above, a configuration is possible in which the measurement cycle determination unit is configured to determine a second cycle shorter than the first cycle for the measurement cycle when the width of the crack is less than or equal to a second threshold value; and determine a third cycle shorter than the second cycle for the measurement cycle when the width of the crack is greater than the second threshold value.

With the measurement cycle determination device described above, a configuration is possible in which the measurement cycle determination unit further includes a second judgment unit configured to determine the second cycle for the measurement cycle when the total value is greater than the first threshold value and the width of the crack is less than or equal to the second threshold value; and determine the third cycle for the measurement cycle when the total value is greater than the first threshold value and the width of the crack is greater than the second threshold value.

With the measurement cycle determination device described above, a configuration is possible in which the measurement cycle information includes at least one of the measurement cycle, a date when next measuring the width of the crack, and an alert indicating that a date for measuring the width of the crack is closer than a predetermined date threshold value.

The measurement cycle determination device described above may further include a memory unit configured to store the measurement cycle information for each of a plurality of structures; a measurement path information generation unit configured to generate, on the basis of the measurement cycle information stored by the memory unit and positional relationship information indicating a positional relationship of each of the plurality of structures, measurement path information including a path for when measuring a width of a crack of each of the plurality of structures; and a measurement path output unit configured to output a measurement path signal indicating the measurement path information.

The measurement cycle determination device described above may further include a memory unit configured to store the measurement cycle information for each crack that has occurred in each of the plurality of structures; a weighting unit configured to weight each of the cracks on the basis of the measurement cycle information; and a weighting signal output unit configured to output a weighting signal indicating the weighting.

A measurement cycle determination method according to another embodiment of the present disclosure includes acquiring at least one of geographic information including items related to a geography of a site where a structure is located, weather information including items related to weather at the site, and structure information including items related to the structure; acquiring crack information related to a crack that has occurred in the structure; determining, on the basis of at least one of the geographic information, the weather information, the structure information, and the crack information, a measurement cycle at which to measure a width of the crack; and outputting a measurement cycle signal indicating measurement cycle information related to the determined measurement cycle.

A measurement cycle determination program according to another embodiment of the present disclosure is configured to cause a computer to execute processing including acquiring at least one of geographic information including items related to a geography of a site where a structure is located, weather information including items related to weather at the site, and structure information including items related to the structure; acquiring crack information related to a crack that has occurred in the structure; determining, on the basis of at least one of the geographic information, the weather information, the structure information, and the crack information, a measurement cycle at which to measure a width of the crack; and outputting a measurement cycle signal indicating measurement cycle information related to the determined measurement cycle.

According to the device, method, program, and the like of the present disclosure, a measurement cycle at which to measure cracks that occur in structures formed from concrete or the like can be suitably determined.

BRIEF DESCRIPTION OF THE DRAWING

FIG. 1A is a cross-sectional view of the sheet before deformation. FIG. 1B is a cross-sectional view of the sheet after deformation.

FIG. 13 is a drawing illustrating an example of information recorded in the processing of S104 depicted in FIG. 6.

FIG. 15 is a drawing illustrating an example of information recorded in the processing of S107 depicted in FIG. 6.

FIG. 18 is drawing illustrating an example of a table containing criteria used in quantification processing by the quantification unit depicted in FIG. 5.

FIG. 19 is a drawing illustrating an example of measurement information updated in the processing of S112 depicted in FIG. 6.

FIG. 26 is a drawing illustrating an example of information updated in the processing of S607 depicted in FIG. 20.

DETAILED DESCRIPTION

Embodiments of the present disclosure will be described hereinafter while referencing the drawings. However, it should be understood that the present disclosure is not limited to the drawings or the following embodiments.

Aspect of Sheet Used in the Present Disclosure

Figure 1A:
FIGS. 1A and 1B are cross-sectional views of a sheet used in the embodiments.
Figure 1B:

FIGS. 1A and 1B are drawings illustrating an aspect of a sheet used in the present embodiment and, in an example thereof, illustrate a state in which a sheet 101 is affixed to a wall surface of a structure, namely a measurement subject 102, in which a crack has occurred. The sheet 101 includes a deformation conforming section 111, a deformation non-conforming section 112, and a deformation buffer portion 113 interposed between the deformation conforming section 111 and the deformation non-conforming section 112. In a typical aspect, as illustrated in FIGS. 1A and 1B, the deformation conforming section and the deformation non-conforming section of the sheet include a first and second main surface of the sheet, respectively.

In the present disclosure, the deformation conforming section is a section that has the ability to deform so as to follow deformation of a measurement subject when an amount of deformation occurs in the measurement subject in a state where the sheet is fixed to the measurement subject.

In the present disclosure, the deformation non-conforming section is a section that substantially does not follow deformation when deformation occurs in the deformation conforming section and, accordingly, is a region where deformation substantially does not occur.

In the present disclosure, the deformation buffer portion is a section that has deformation buffering capacity sufficient to ensure that the deformation non-conforming section substantially does not deform as a result of the deformation of the deformation conforming section.

The sheet may be constituted by a single layer or multiple layers. The sheet need only include sections functioning as a deformation conforming section, a deformation non-conforming section, and a deformation buffer section. Accordingly, in an exemplary aspect, the sheet is a single layer including a deformation conforming section, a deformation non-conforming section, and a deformation buffer section by being imparted with suitable thicknesses and physical properties. In another exemplary aspect, the sheet is constituted by multiple layers of different materials, thicknesses, and the like, each of the layers being capable of functioning as a deformation conforming section, a deformation non-conforming section, and a deformation buffer section, respectively. In yet another exemplary aspect, the sheet can be constituted by two layers, one functioning as a deformation conforming section and a deformation buffer section and one functioning as a deformation non-conforming section, or one functioning as a deformation conforming section and one functioning as a deformation buffer section and a deformation non-conforming section. As discussed above, the layer configuration of the sheet can be designed as desired on the condition that the sheet includes sections that function as a deformation conforming section, a deformation non-conforming section, and a deformation buffer section. For example, FIGS. 1A and 1B illustrate an example of a case in which the sheet is a single layer, and in other examples, the sheet is in three layers, namely a stretchable layer, an unstretchable layer, and a viscoelastic layer.

The deformation conforming section has a first pattern that includes a plurality of straight lines extending in a first direction; and the deformation non-conforming section has a second pattern that includes a plurality of straight lines extending in a second direction different than the first direction. The sheet of the present disclosure is configured so as to enable the detection of moiré fringes produced by the first pattern and the second pattern. More specifically, the first pattern is viewable via the second pattern. Here, "the first pattern is viewable via the second pattern" means that the first pattern can be visualized along with the second pattern when the first and second patterns are observed from a second pattern side among a first pattern side and the second pattern side of the sheet. Means for the visualization can be selected as desired, and examples thereof include pattern imaging under visible light using various types of cameras. According to a configuration in which the first pattern is viewable via the second pattern, the moiré fringes produced by the interference between the first pattern and the second pattern are also viewable, and evaluation of three-dimensional deformation of the measurement subject, based on the moiré fringes, is possible.

In a preferable aspect in which the first pattern is viewable via the second pattern, the section of the sheet of the present disclosure from the first pattern, via the second pattern, to the sheet surface, is typically formed from a clear material.

In the present disclosure, "transparent material" refers to a material having a total optical transmittance of at least 30% at light wavelengths of 300 to 830 nm, more preferably at least 80%. The total optical transmittance is the value for total light transmission as measured using a haze meter (such as an NDH 2000 haze meter, manufactured by Nippon Denshoku Industries Co., Ltd. (Bunkyo Ward, Tokyo)).

One essential characteristic of the sheet of the present disclosure is that the first pattern becomes strained due to deformation of the deformation conforming section, and that the second pattern that the deformation non-conforming section has is substantially not affected by the strain in the first pattern, that is, substantially does not become strained. When the sheet has been fixed to a measurement subject, deformation of the measurement subject can be detected in three dimensions by the strain in the first pattern image. That is, deformation in an in-plane direction of the measurement subject such as illustrated in FIGS. 1A and 1B (FIG. 1A illustrates pre-deformation, and FIG. 1B illustrates post-deformation) causes strain in the first pattern to occur. Moreover, by detecting and analyzing the moiré fringes produced by the strain in the first pattern and the unstrained second pattern, deformation that has occurred in the measurement subject can be quantitatively evaluated in three dimensions. Additionally, positions at which the deformation has occurred in the measurement subject can be identified.

When evaluating the deformation in the measurement subject using the sheet of the present disclosure, the moiré fringes of the sheet are detected. The sheet according to the present disclosure offers the advantage that evaluation can be conveniently performed in that the device used to detect the moiré pattern need not necessarily be brought within the vicinity of the sheet. In addition, the sheet of the present disclosure is inexpensive and does not require a power source or the like and, therefore, has the advantage of being easily installed.

Any conventionally publicly known patterns used for evaluating deformation by moiré fringes can be used as the first pattern and the second pattern. The details of the patterns, for example, the type of pattern shape, pitch, and the like may be appropriately selected depending on the amount of deformation of the target or the like. Examples of the pattern shape include grids, staggered patterns, dots, a plurality of parallel strait lines, and the like. In an illustrative aspect, the first and second patterns can each be a grid having a width of about 0.2 to about 0.4 mm and a pitch of about 0.4 to about 0.8 mm. For example, when evaluating deformation of a wall of a structure or the like, which is a preferred use of the sheet according to the present disclosure, detection of deformation of about 0.1 to 2.0 mm is often desired. An example of a pattern shape and pitch suited to such a usage is a sheet, one side of which is about 100 mm long, having a pitch of about 0.3 to about 1.0 mm.

The detailed structure of the sheet according to this aspect of the present embodiment is described in, for example, Japanese Unexamined Patent Application Publication No. 2015-184043A and the like.

Aspects of the First Pattern and the Second Pattern

Figure 2A:
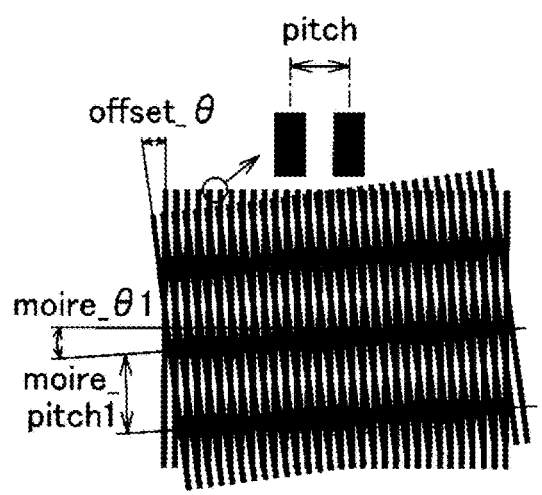
FIG. 2A is a partially exploded plan view of the sheet before a deformation conforming section deforms.
Figure 2B:
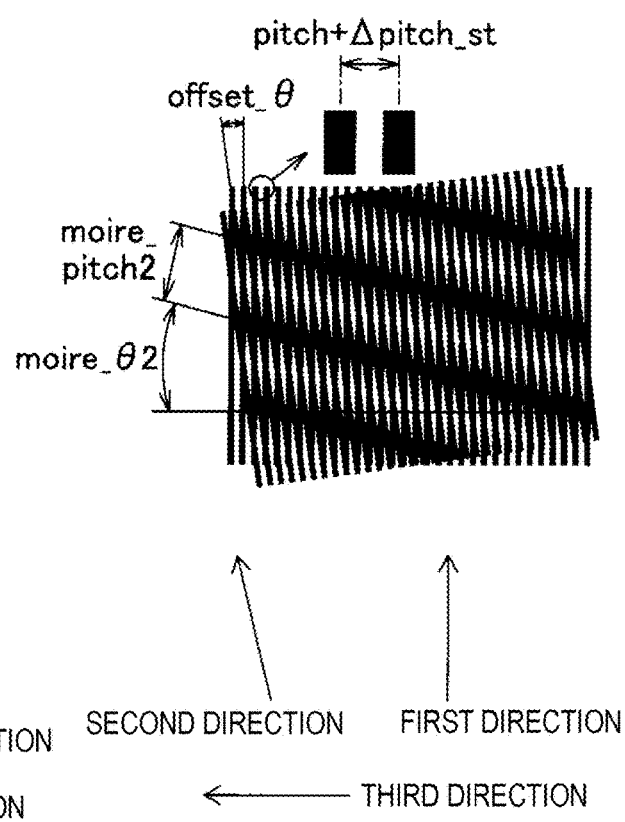
FIG. 2B is a partially exploded plan view of the sheet after the deformation conforming section has deformed.

FIG. 2A is a partially exploded plan view of the sheet 101 before the deformation conforming section 111 deforms. FIG. 2B is a partially exploded plan view of the sheet 101 after the deformation conforming section 111 has deformed.

A pitch of a plurality of straight lines arranged in parallel and included in each of the first pattern 121 and the second pattern before the deformation conforming section 111 deforms is referred to as the "pitch." After the deformation conforming section 111 has deformed, the pitch of the straight lines included in the first pattern 121 change to "pitch+Δpitch_st." The deformation non-conforming section 112 does not deform and, therefore, even after the deformation conforming section 111 has deformed, the pitch of the straight lines included in the first pattern 121 is maintained as pitch.

A pitch of the moiré before the deformation conforming section 111 deforms is referred to as a first pitch moiré_pitch1, and an angle of inclination between a third direction orthogonal to the first direction of the moiré before the deformation conforming section 111 deforms and the extending direction of the moiré is referred to as a first angle of inclination moiré_$\theta$1. A pitch of the moiré after the deformation conforming section 111 has deformed is referred to as a second pitch moiré_pitch2, and an angle of inclination between the third direction after the deformation conforming section 111 has deformed and the extending direction of the moiré is a second angle of inclination moiré_$\theta$2.

Figure 3:
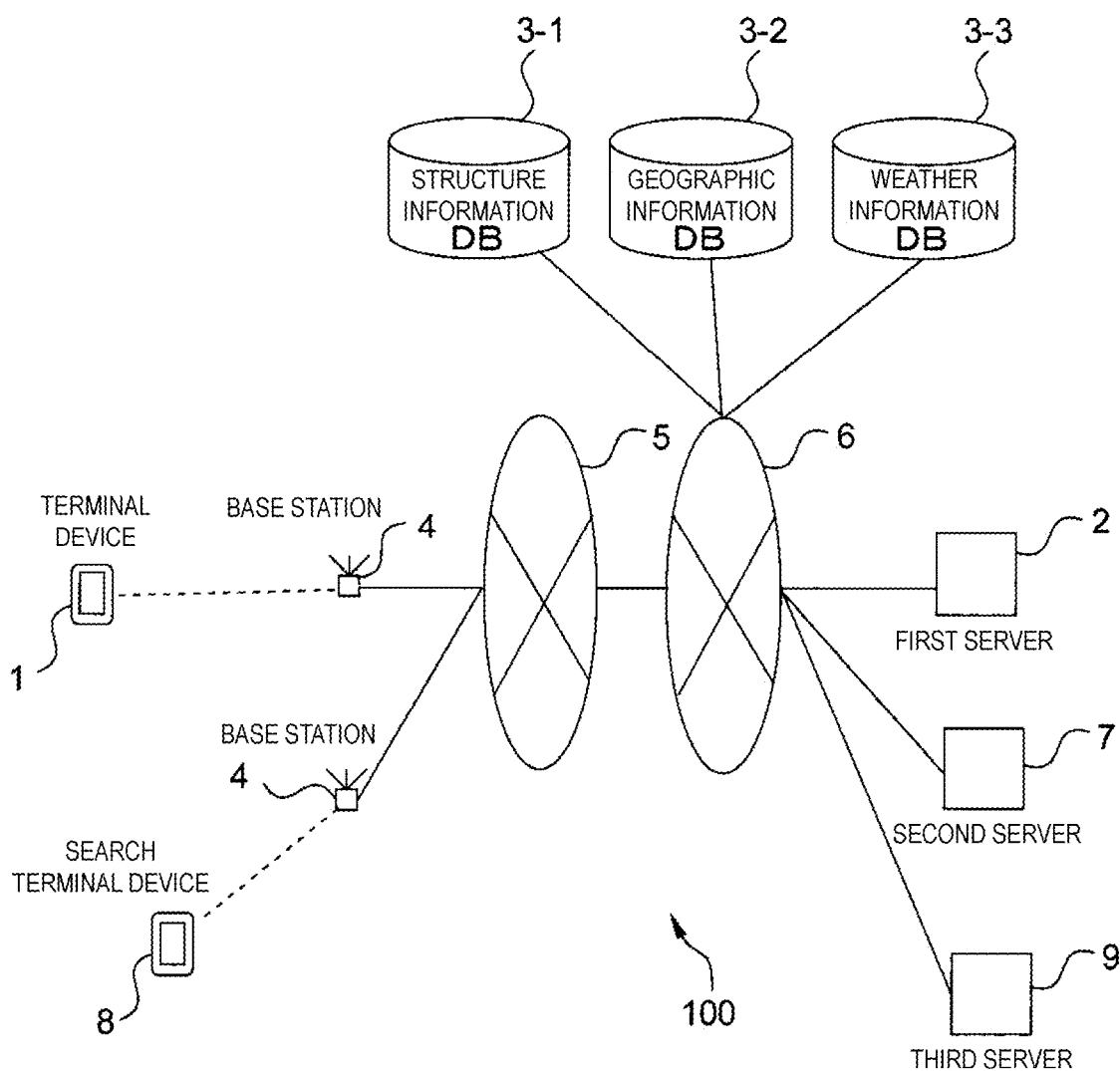
FIG. 3 is a drawing illustrating a measurement cycle determination system according to the embodiments.

Configuration and Function of Measurement Cycle Determination System According to the Embodiment FIG. 3 is a drawing illustrating a measurement cycle determination system according to the embodiment.

In a measurement cycle determination system 100, switching equipment (not illustrated) is mutually connected via a wide area communications network, namely a communications network 5. The switching equipment connects a wireless communications network that covers a certain area to the communications network 5. A base station 4 is disposed in the wireless communications network to administer a wireless zone covering the area. The base station 4 is connected to the switching equipment via a wireless network control device (not illustrated) to which the base station 4 belongs. Moreover, when a terminal device 1 and a search terminal device 8 within the area perform communication with a first server 2, a second server 7, and a third server 9 or the like, the terminal device 1 and the search terminal device 8 are connected to the switching equipment via the base station 4 and are also connected to the communications network 5.

Additionally, the communications network 5 is connected to an internet 6 via a gateway (not illustrated), by means of a wired LAN or similar Ethernet (trade name). Furthermore, a structure information database 3-1, a geographic information database 3-2, and a weather information database 3-3, as well as the first server 2, the second server 7, and the third server 9 are connected to the internet 6. The geographic information database 3-2 is a database in which geographic information of each site is stored.

The terminal device 1 is a terminal device used by an inspector in the first to third embodiments, and the search terminal device 8 is a terminal device used by a general user in the third embodiment. The first server 2 is a server used in the first embodiment, the second server 7 is a server used in the second embodiment, and the third server 9 is a server used in the third embodiment.

The structure information database 3-1 stores, for each structure, structure information including items related to structures such as the construction year, the material of the structure such as reinforced concrete, and the type of structure such as bridge or tunnel. The structure information database 3-1 may be stored in a single storage device, or may be stored in a plurality of storage devices according to the type of structure information that is stored.

The geographic information database 3-2 stores, for each structure, geographic information including items related to the geography of the site where the structure is located such as ground strength, presence/absence of salt damage, the highest seismic intensity of earthquakes that have occurred, the frequency of earthquakes. The geographic information database 3-2 may be stored in a single storage device, or may be stored in a plurality of storage devices according to the type of geographic information that is stored.

The weather information database 3-3, for each region, weather information including items related to the weather at the site where the structure is located such as the highest temperature, lowest temperature, highest humidity, lowest humidity, maximum wind speed, maximum rainfall, and maximum snowfall. The weather information database 3-3 may be stored in a single storage device, or may be stored in a plurality of storage devices according to the type of weather information that is stored.

Configuration of the Measurement Cycle Determination System According to the First Embodiment A measurement cycle determination system according to the first embodiment includes the terminal device 1, the first server 2, the structure information database 3-1, the geographic information database 3-2, and the weather information database 3-3 illustrated in FIG. 3.

Figure 4:
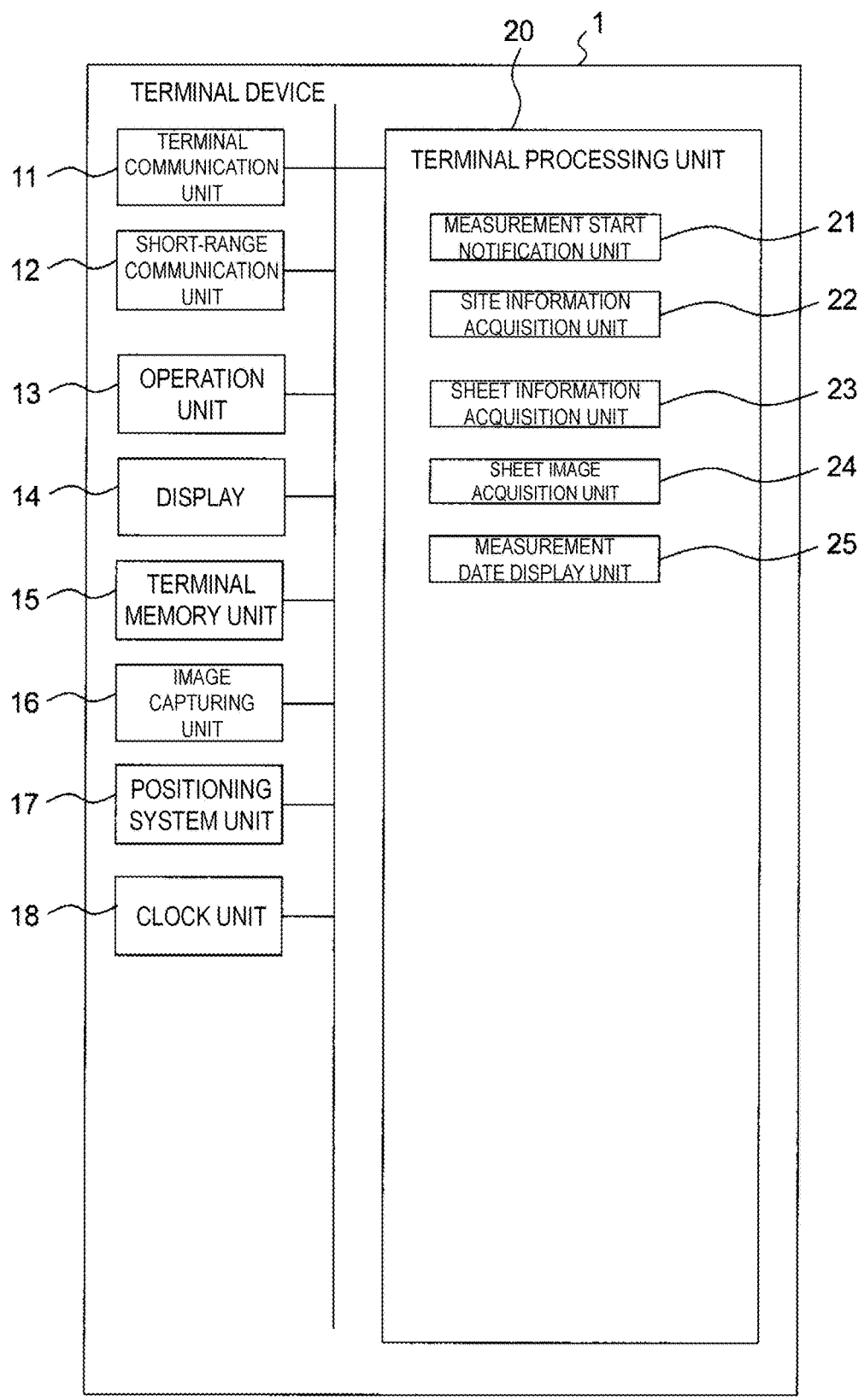
FIG. 4 is a drawing illustrating one example of a schematic configuration of the terminal device depicted in FIG. 3.

Configuration and Function of the Terminal Device According to the First Embodiment FIG. 4 is a drawing illustrating an example of a schematic configuration of the terminal device 1.

The terminal device 1 is a multifunctional mobile phone (i.e. a smartphone), and is capable of connecting to a wireless communication network, short-range communication, executing predetermined application programs, and the like. In order to realize these capabilities, the terminal device 1 includes a terminal communication unit 11, a short-range communication unit 12, an operation unit 13, a display 14, a terminal memory unit 15, an image capturing unit 16, a positioning system unit 17, a clock unit 18, and a terminal processing unit 20. Note that the terminal device 1 may be any communication device that has communication functions and, for example, may be a terminal device such as a personal digital assistant (PDA), a mobile gaming device, a portable music player, or a tablet computer.

The terminal communication unit 11 is provided with a communication interface circuit that includes an antenna designed to primarily operate in the 2.1 GHz receiving band, and connects the terminal device 1 to a communication network. The terminal communication unit 11 establishes a wireless signal line with a base station (not illustrated) by a code division multiple access (CDMA) or similar method via a channel allocated by the base station to wirelessly communicate with the base station. Moreover, the terminal communication unit 11 supplies data received from the base station to the terminal processing unit 20. Additionally, the terminal communication unit 11 sends data supplied from the terminal processing unit 20 to the base station. Note that the terminal communication unit 11 preforms data communication with a server (not illustrated) in accordance with hypertext transfer protocol (HTTP). Additionally, the terminal communication unit 11 is provided with a communication interface circuit that includes an antenna designed to primarily operate in the 2.4 GHz receiving band, and that bypasses the base station and performs wireless communication via Wi-Fi (trade name) or a similar a wireless LAN base station.

The short-range communication unit 12 is provided with an interface circuit for performing short-range wireless communication in accordance with Bluetooth LE (Low Energy) (trade name) or a similar communication system, and performs short-range wireless communication with other terminal devices and the like. Moreover, the short-range communication unit 12 supplies data received from the other terminal devices and the like to the terminal processing unit 20. Additionally, the short-range communication unit 12 sends data supplied from the terminal processing unit 20 to the other terminal devices and the like. Note that the short-range communication unit 12 may be provided with an interface circuit for performing short-range wireless communication in accordance with Bluetooth (trade name), Radio Frequency Identification (RFID), ZigBee or a similar communication system.

The operation unit 13 may be any device provided that operation of the terminal device 1 is possible, and examples thereof include keyboards and the like. A user can use this device to input characters, numbers, and the like. The operation unit 13 receives commands from the user, generates signals corresponding to the received commands, and outputs the signals to the terminal processing unit 20. Additionally, the operation unit 13 receives commands of the user by contact such as tapping, dragging, flicking, generates signals corresponding to the received commands, and outputs the signals to the terminal processing unit 20.

The display 14 may be any device, provided that output of video images, still images, and the like is possible. The display 14 displays video images corresponding to video image data, still images corresponding to still image data, and the like supplied from the terminal processing unit 20.

The terminal memory unit 15 is provided with, for example, semiconductor memory. The terminal memory unit 15 stores driver programs, operating system programs, application programs, data, and the like used in the processing by the terminal processing unit 20. For example, as driver programs, the terminal memory unit 15 stores driver programs such as a mobile phone communication device driver program and a wireless LAN communication device driver program for controlling the terminal communication unit 11. Additionally, the terminal memory unit 15 stores a short-range wireless communication device driver program for controlling the short-range communication unit 12, an input device driver program for controlling the operation unit 13, an output device driver program for controlling the display 14, and the like. Additionally, the terminal memory unit 15 stores application programs such as various programs including web browser programs for acquiring and displaying web pages. The computer programs may be installed in the terminal memory unit 15 using a publicly known setup program or the like, from a computer-readable portable recording medium such as semiconductor memory that includes flash memory or the like.

Additionally, the terminal memory unit 15 stores data such as information and data used in image capture processing and deformation amount measuring processing, and data required for image capture processing and deformation amount measuring processing. Furthermore, the terminal memory unit 15 may temporarily store temporary data pertaining to a predetermined processing.

The image capturing unit 16 is provided with imaging elements disposed in an array, and an element driving unit for driving the imaging elements. The imaging elements include a charge-coupled device (CCD) sensor or an active pixel sensor (APS), and a color filter, and accumulate charge corresponding to incident light. The element driving unit converts the charges accumulated in each of the imaging elements into electrical signals and outputs these electrical signals to the terminal processing unit 20.

The positioning system unit 17 measures a position where the terminal device 1 exists, in accordance with commands from the terminal processing unit 20. The positioning system unit 17 is provided with a GPS circuit that includes an antenna designed to primarily operate in the 1.5 GHz receiving band, and receives GPS signals from a GPS satellite (not illustrated). The positioning system unit 17 decodes the GPS signals and acquires time information and the like. The positioning system unit 17 calculates a pseudo-distance from the GPS satellite to the positioning system unit 17 on the basis of the time information and the like, determines the position (latitude, longitude, and the like) where the terminal device 1 exists by solving a system of equations obtained by substituting the pseudo-distance, and outputs the position as position information.

The clock unit 18 is constituted by a clock circuit or the like, counts the date and time, and generates date information and time information for the update processing of various types of information.

The terminal processing unit 20 is provided with one or a plurality of processors and peripheral circuits thereof. The terminal processing unit 20 integrally controls the overall operations of the terminal device 1 and, for example, is a central processing unit (CPU). The terminal processing unit 20 controls the operations of the terminal communication unit 11, the short-range communication unit 12, and the like so that the various processes of the terminal device 1 are executed with appropriate procedures corresponding to the programs stored in the terminal memory unit 15, the operations of the operation unit 13, and the like. The terminal processing unit 20 executes processing on the basis of the programs (the driver programs, the operating system programs, the application programs, and the like) stored in the terminal memory unit 15. Additionally, the terminal processing unit 20 can execute a plurality of programs (the application programs and the like) in parallel.

The terminal processing unit 20 includes a measurement start notification unit 21, a site information acquisition unit 22, a sheet information acquisition unit 23, a sheet image acquisition unit 24, and a measurement date display unit 25. Each of the units of the terminal processing unit 20 is a functional module that is implemented by a program executed on the processor of the terminal processing unit 20. Alternatively, each of the units that is provided in the terminal processing unit 20 may be implemented in the terminal device 1 as an independent integrated circuit, microprocessor, or firmware.

Figure 5:
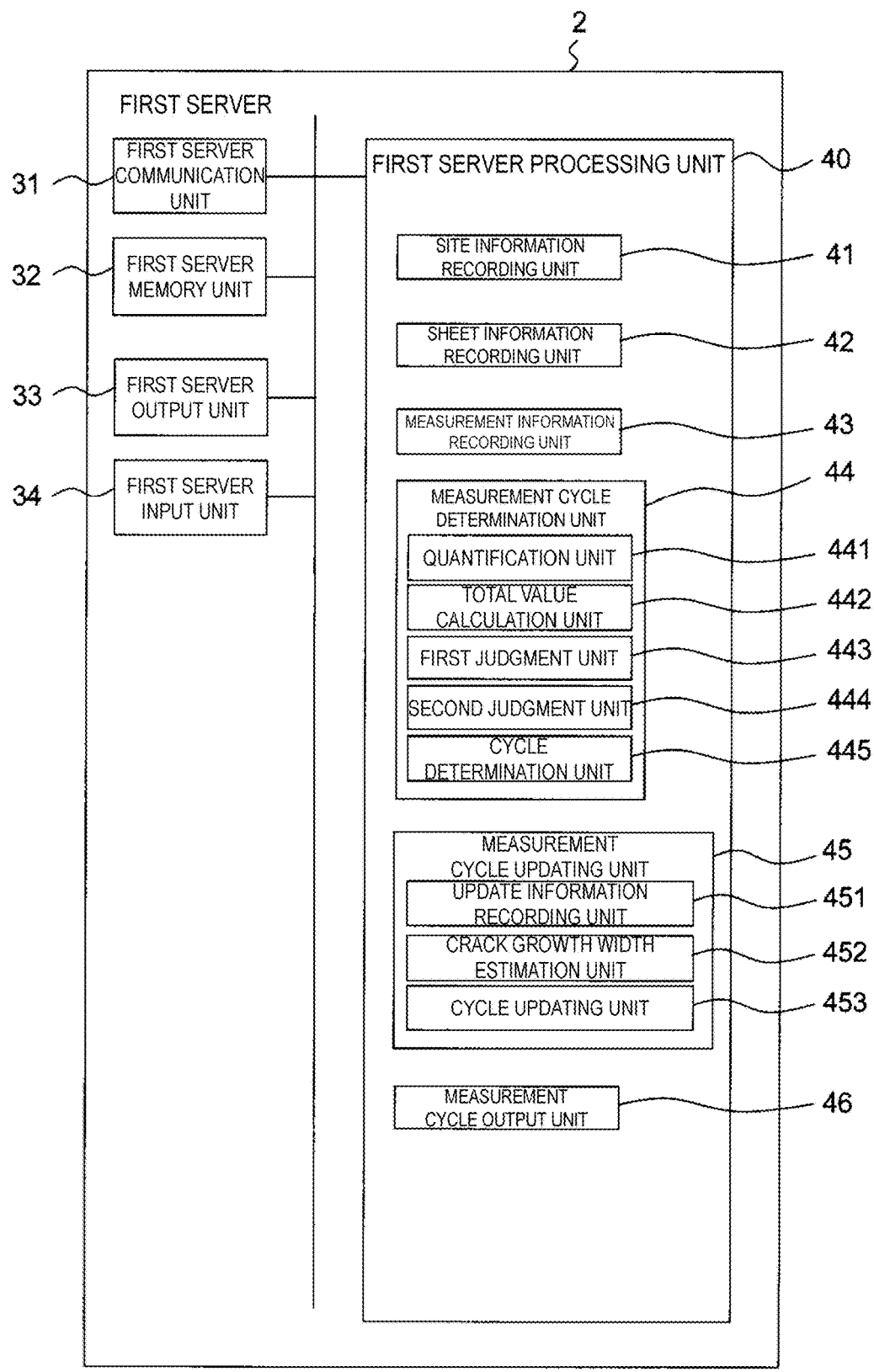
FIG. 5 is a drawing illustrating one example of a schematic configuration of the first server depicted in FIG. 3.

Configuration and Function of the First Server According to the First Embodiment FIG. 5 is a drawing illustrating an example of a schematic configuration of an example of the measurement cycle determination device according to the first embodiment, namely the first server 2.

The first server 2 is an information processing device capable of various types of information processing, and is provided with a first server communication unit 31, a first server memory unit 32, a first server output unit 33, a first server input unit 34, and a first server processing unit 40.

The first server communication unit 31 includes a wired communication interface circuit such as an Ethernet (trade name). The first server communication unit 31 performs communication with the terminal device 1, the structure information database 3-1, the geographic information database 3-2, the weather information database 3-3, and the like via a LAN (not illustrated in the drawings) and the internet 6. Moreover, the first server communication unit 31 supplies data received from the terminal device 1, the structure information database 3-1, the geographic information database 3-2, the weather information database 3-3, and the like to the first server processing unit 40. Additionally, the first server communication unit 31 sends data supplied from the first server processing unit 40 to the terminal device 1 and the like.

The first server memory unit 32 includes at least one of, for example, semiconductor memory, a magnetic disk device, and an optical disk device. The first server memory unit 32 stores driver programs, operating system programs, application programs, data, and the like used in the processing by the first server processing unit 40. For example, the first server memory unit 32 stores driver programs such as a communication device driver program for controlling the first server communication unit 31, and the like. Additionally, the first server memory unit 32 stores operating system programs such as connection control programs by communication protocol such as Transmission Control Protocol/Internet Protocol (TCP/IP). Additionally, the first server memory unit 32 stores application programs such as data processing programs for sending/receiving various types of data. The computer programs may be installed in the first server memory unit 32 using a publicly known setup program or the like, from a computer-readable portable recording medium such as, for example, a CD-ROM, or a DVD-ROM.

The first server output unit 33 may be any device provided that output of video images, still images, and the like is possible, and examples thereof include touch panel display devices, liquid crystal displays, organic electro-luminescence (EL) displays, and the like. The first server output unit 33 displays video images corresponding to video image data, still images corresponding to still image data, and the like supplied from the first server processing unit 40.

The first server input unit 34 may be any device provided that input to the first server 2 is possible, and examples thereof include touch panel input devices, keypads, and the like. A user can use this device to input characters, numbers, and the like. The first server input unit 34 receives commands from the user, generates signals corresponding to the received commands, and outputs the signals to the first server processing unit 40.

The first server processing unit 40 is provided with one or a plurality of processors and peripheral circuits thereto. The first server processing unit 40 integrally controls the overall operations of the first server 2 and, for example, is a CPU. The first server processing unit 40 controls the operations of the first server communication unit 31 and the like so that the various processes of the first server 2 are executed with appropriate procedures corresponding to the programs and the like stored in the first server memory unit 32. The first server processing unit 40 executes processing on the basis of the programs (the driver programs, the operating system programs, the application programs, and the like) stored in the first server memory unit 32. Additionally, the first server processing unit 40 can execute a plurality of programs (the application programs and the like) in parallel.

The first server processing unit 40 includes a site information recording unit 41, a sheet information recording unit 42, a measurement information recording unit 43, a measurement cycle determination unit 44, a measurement cycle updating unit 45, and a measurement cycle output unit 46. The measurement cycle determination unit 44 includes a quantification unit 441, a total value calculation unit 442, a first judgment unit 443, a second judgment unit 444, and a cycle determination unit 445. The measurement cycle updating unit 45 includes an update information recording unit

451, a crack growth width estimation unit 452, and a cycle update unit 453. Each of the units of the first server processing unit 40 is a functional module that is implemented by a program executed on the processor of the first server processing unit 40. Alternatively, each of the units that is provided in the first server processing unit 40 may be implemented in the first server 2 as an independent integrated circuit, microprocessor, or firmware.

Figure 6:
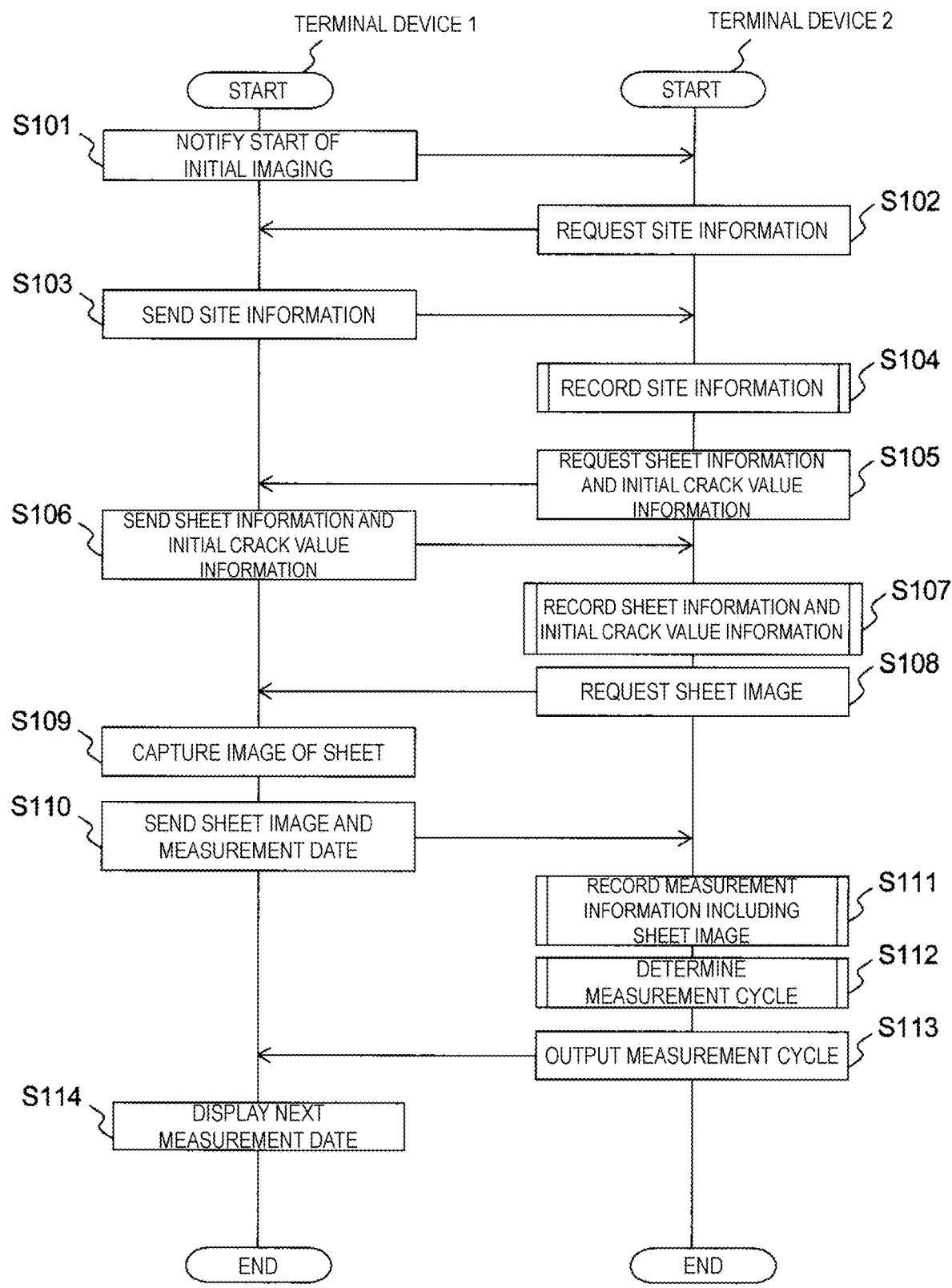
FIG. 6 is a flowchart illustrating an example of measurement cycle determination processing at a time of initial imaging by the measurement cycle determination system depicted in FIG. 3.

Measurement Cycle Determination Processing by the Measurement Cycle Determination System According to the First Embodiment FIG. 6 is a flowchart illustrating an example of measurement cycle determination processing executed by the measurement cycle determination system 100.

First, on the basis of a command of an inspector (not illustrated in the drawings), the terminal device 1 notifies the first server 2 that initial imaging of a crack on which the sheet is affixed has started (S101). Further details thereof are described using FIG. 7.

Figure 7:
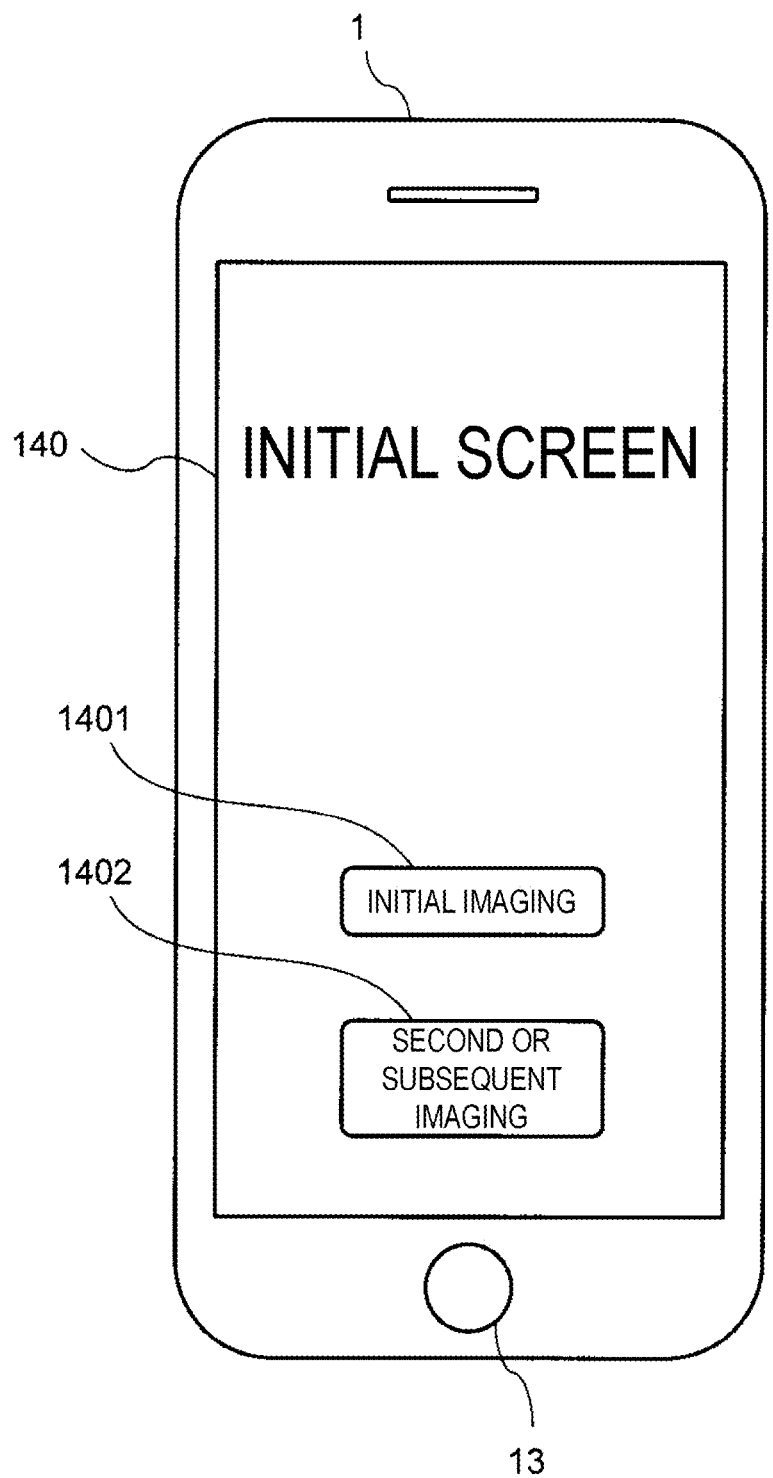
FIG. 7 is drawing illustrating an example of an initial screen displayed on the terminal device.

Upon selection, via the display 14, of an application program for executing crack measurement processing, the measurement start notification unit 21 displays an initial screen on the display 14. FIG. 7 is drawing illustrating an example of the initial screen displayed on the display 14.

The initial screen 140 includes an initial imaging button 1401 and a second or subsequent imaging button 1402. When an inspector (not illustrated in the drawings) presses the initial imaging button 1401 of the initial screen 140, the measurement start notification unit 21 of the terminal device 1 notifies the first server 2 to start initial imaging of the crack on which the sheet is affixed (S101).

Upon being notified to start of the initial imaging of the crack on which the sheet is affixed, the site information recording unit 41 of the first server 2 requests site information from the terminal device 1 (S102). Upon receipt of the request for site information, the site information acquisition unit 22 of the terminal device 1 acquires the site information and sends a signal indicating the acquired site information to the first server 2 (S103).

Figure 8:
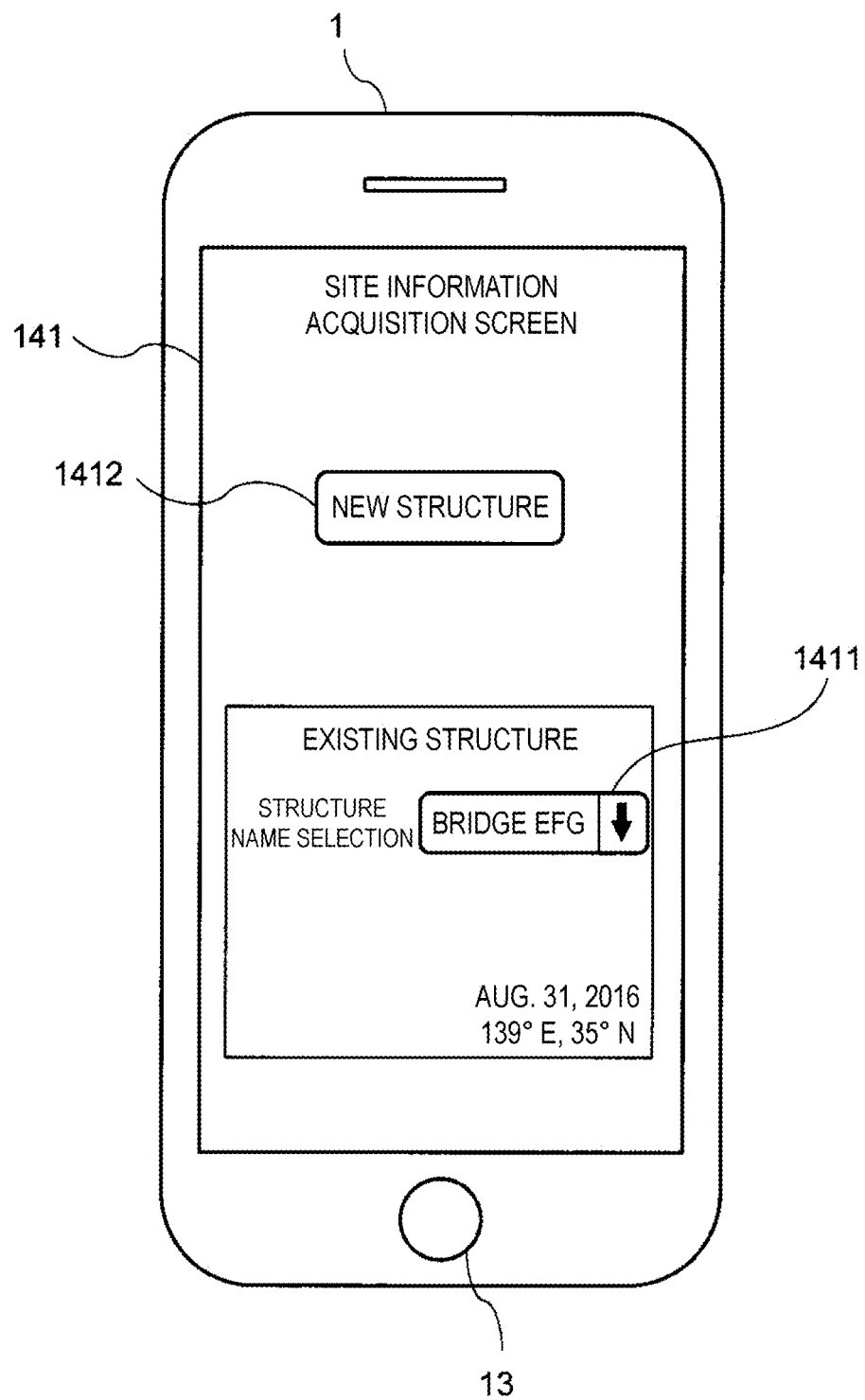
FIG. 8 is drawing illustrating an example of a (first) site information acquisition screen displayed on the terminal device.
Figure 9:
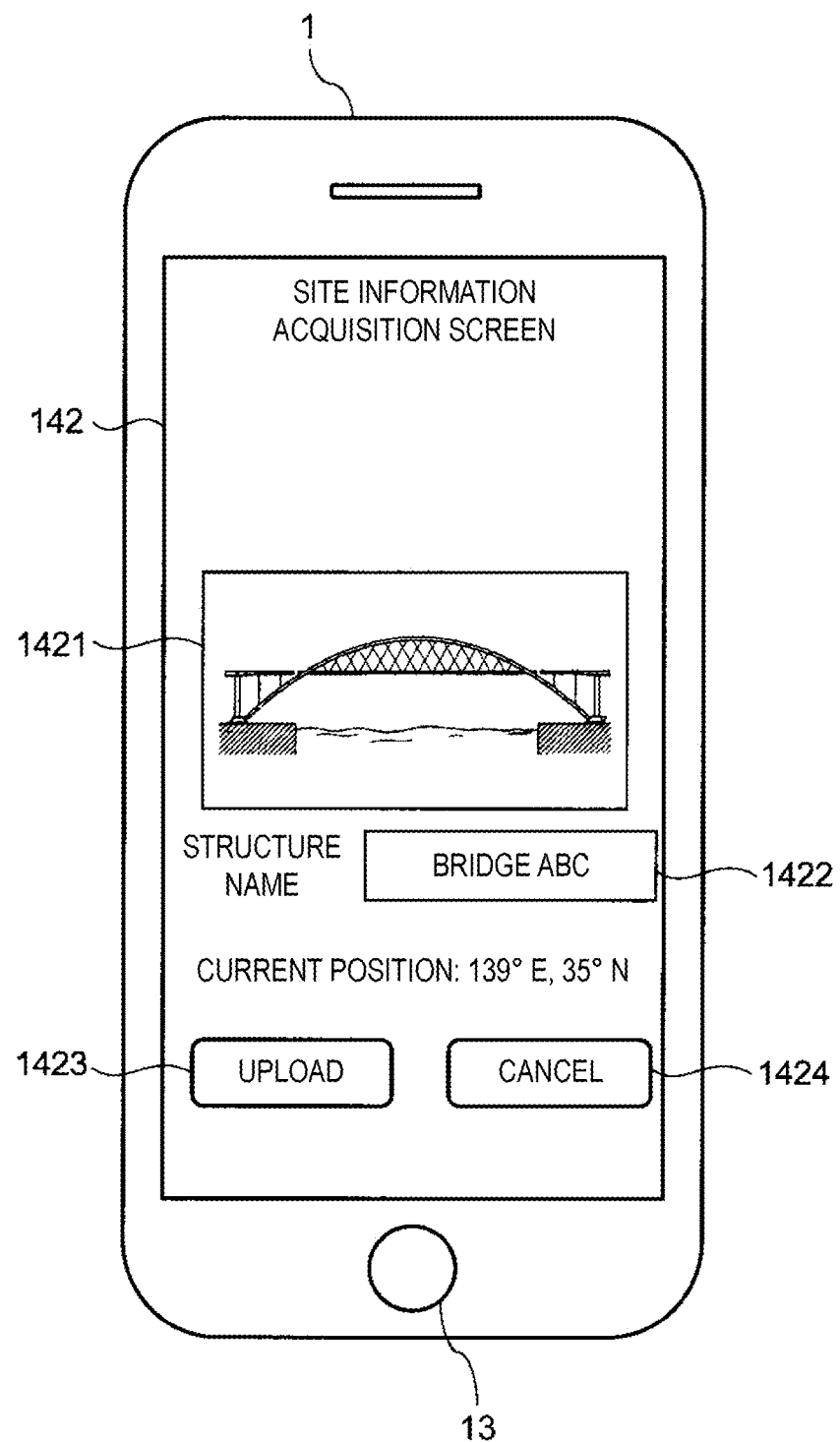
FIG. 9 is drawing illustrating an example of a (second) site information acquisition screen displayed on the terminal device.

FIGS. 8 and 9 are drawings illustrating an example of a site information acquisition screen displayed on the display 14 whereby the terminal device 1, which received the request in S102, acquires and sends the site information in S103. Specifically, FIG. 8 illustrates an example of a first site information acquisition screen, and FIG. 9 illustrates an example of a second site information acquisition screen.

Upon receipt of a request for site information, the site information acquisition unit 22 displays a first site information acquisition screen 141 on the display 14. The first site information acquisition screen 141 includes an existing structure selection section 1411 and a new structure selection section 1412.

When the existing structure selection section 1411 is pressed, the site information acquisition unit 22 displays names of recorded structures in drop down list format and in a selectable manner on the display 14. Upon selection of a name of a structure displayed in the drop down list format by the site information acquisition unit 22, the site information acquisition unit 22 sends a signal indicating site information including the name of the selected structure to the first server 2 (S103).

When the new structure selection section 1412 in the first site information acquisition screen 141 is pressed, the site information acquisition unit 22 displays a second site information acquisition screen 142 on the display 14. The second site information acquisition screen 142 includes a structure drawing image 1421, a structure name input section 1422, an upload button 1423, and a cancel button 1424 that erases inputted information. The structure drawing image 1421 is acquired in advance by the inspector (not illustrated in the drawings) operating the terminal device 1, and is stored in the terminal memory unit 15. When the structure name input section 1422 is pressed, the site information acquisition unit 22 displays an input screen on the display 14, and the name of the structure is input via the operation unit 13 by the inspector (not illustrated in the drawings). When the upload button 1423 is pressed, the site information acquisition unit 22 sends a signal indicating site information including the structure drawing image 1421, the name of the structure input in the structure name input section 1422, and position information acquired by the positioning system unit 17 to the first server 2 (S103).

Next, the site information recording unit 41 of the first server 2 records the site information sent from the terminal device 1 (S104). Upon recording of the site information sent from the terminal device 1, the sheet information recording unit 42 of the first server 2 requests sheet information and initial crack value information from the terminal device 1 (S105). Upon receipt of the request for the sheet information and the initial crack value information, the sheet information acquisition unit 23 of the terminal device 1 acquires the sheet information and the initial crack value information and sends signals indicating each of the acquired sheet information and initial crack value information to the first server 2 (S106).

Figure 10:
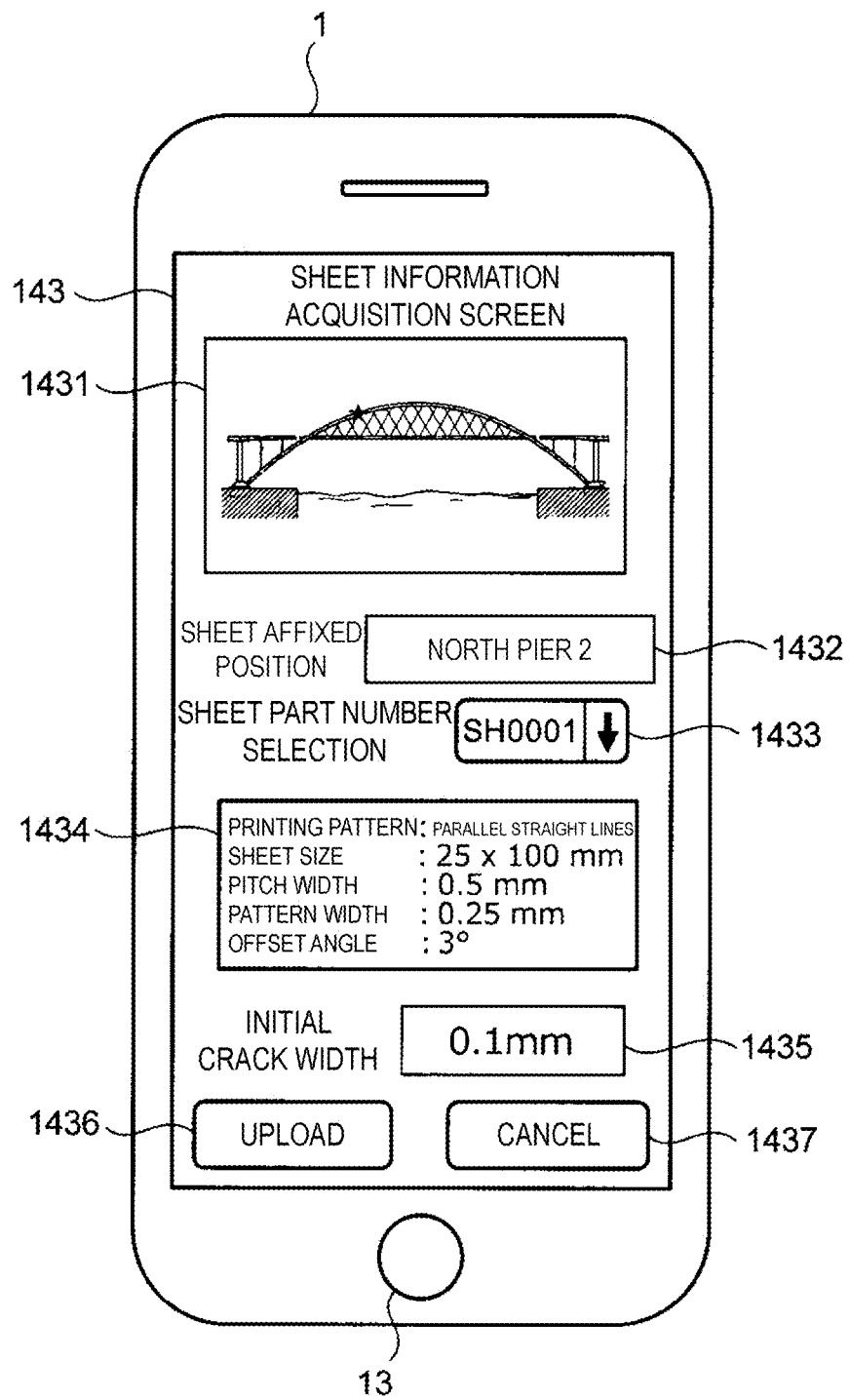
FIG. 10 is drawing illustrating an example of a (first) sheet information acquisition screen displayed on the terminal device.

FIG. 10 is a drawing illustrating an example of a first sheet information acquisition screen displayed on the display 14 whereby the terminal device 1 that has received the request in S105 acquires and sends the sheet information and the initial crack value information.

Upon receipt of a request for sheet information, the sheet information acquisition unit 23 displays a first sheet information acquisition screen 143 on the display 14. The first sheet information acquisition screen 143 includes a sheet position selection section 1431, a sheet position name input section 1432, a sheet part number selection section 1433, a sheet information display section 1434, and an initial crack width input section 1435. The first sheet information acquisition screen 143 also includes an upload button 1436 and a cancel button 1437 that erases inputted information. The sheet position selection section 1431 includes a drawing image of the structure on which the sheet is affixed and, as indicated by the star symbol in FIG. 10, identifies a position on the drawing image of the structure pressed by the inspector (not illustrated in the drawings) as sheet affixed coordinates that indicate the affixed position of the sheet. The drawing image included in the sheet position selection section 1431 may be acquired from the first server 2 or another server (not illustrated in the drawings) via the communications network 5, or photograph data captured by the terminal device 1 may be used. When the sheet position name input section 1432 is pressed, the sheet information acquisition unit 23 displays an input screen on the display 14, and the name of the affixed position of the sheet is input via the operation unit 13 by the inspector (not illustrated in the drawings). When the sheet part number selection section 1433 is pressed, sheet part numbers are displayed in drop down list format and in a selectable manner. Upon selection of a sheet part number displayed in the drop down format in the sheet part number selection section 1433, the sheet information acquisition unit 23 displays pattern information such as a printing pattern corresponding to the selected sheet part number, the pitch width, and the offset angle in the sheet information display section 1434. When the initial crack width input section 1435 is pressed, the sheet information acquisition unit 23 displays an input screen on the display 14, and the initial value of the crack width of the crack on which the sheet is affixed is input via the operation unit 13 by the inspector (not illustrated in the drawings). When the upload button 1436 is pressed, the sheet information acquisition unit 23 sends signals indicating the sheet information including the sheet affixed coordinates, the sheet position name, and the initial crack value information including the initial value of the crack width to the first server 2 (S106). The sheet affixed coordinates are information inputted via the sheet position selection section 1431, and the sheet position name is information inputted via the sheet position name input section 1432. The pattern information is information corresponding to the sheet selected via the sheet part number selection section 1433, and the initial value of the crack width is information inputted via the initial crack width input section 1435.

The sheet information recording unit 42 of the first server 2 records the sheet information and the initial crack value information corresponding to the signals sent from the terminal device 1 (S107). Upon recording the sheet information and the initial crack value information, the sheet information recording unit 42 requests a sheet image from the terminal device 1 (S108). Upon receipt of the request for the sheet image, the sheet image acquisition unit 24 of the terminal device 1 captures an image of the sheet affixed to the crack (S109), and sends image data representing the captured sheet image to the first server 2 (S110).

Figure 11:
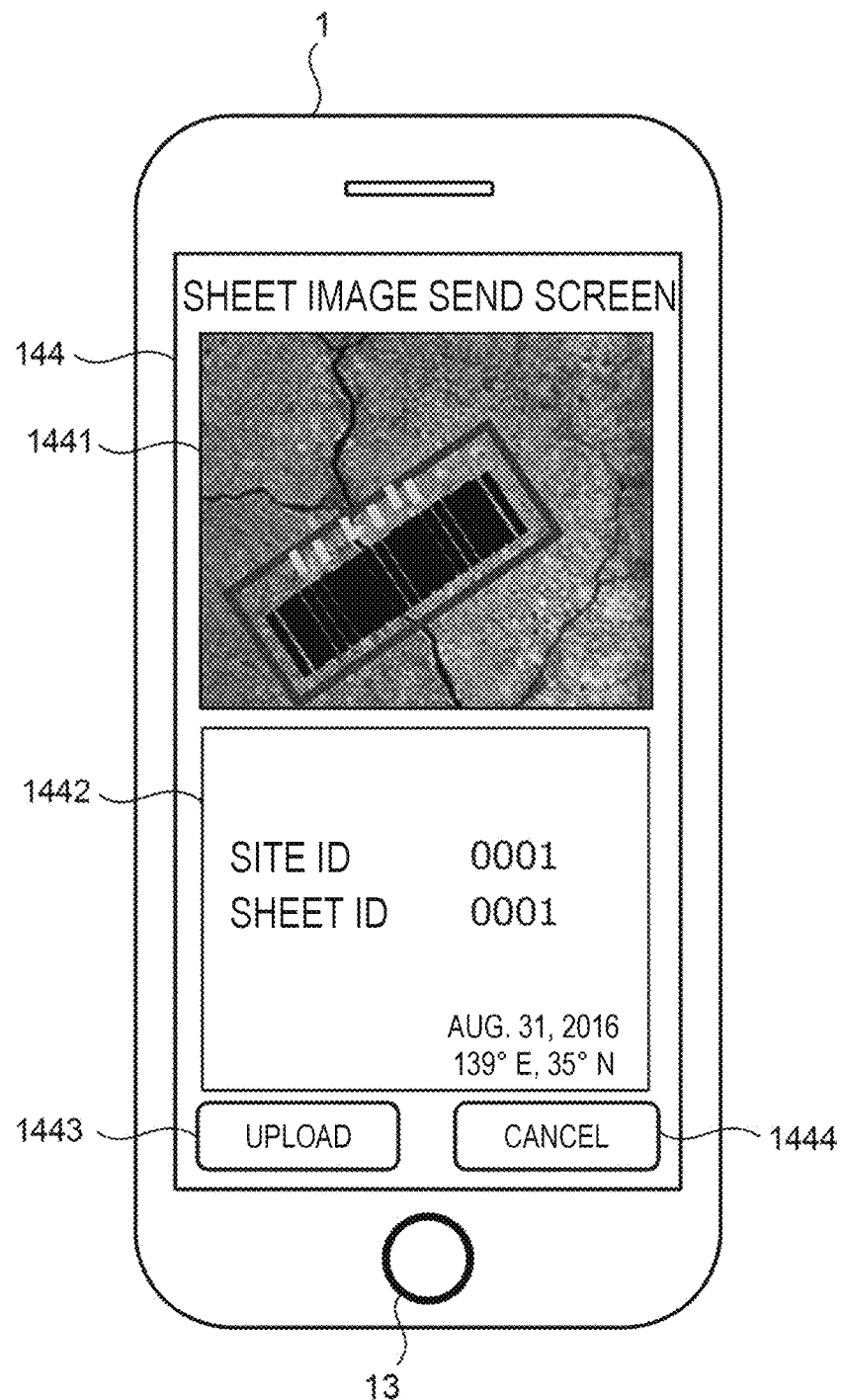
FIG. 11 is drawing illustrating an example of a (first) sheet image send screen displayed on the terminal device.

FIG. 11 is a drawing illustrating an example of a first sheet image send screen displayed on the display 14 whereby the terminal device 1 that has received the request in S108 sends a sheet image acquired at a time of initial imaging in S109 along with the measurement date in S110.

Upon completion of the capturing of the sheet image (S109), the sheet image acquisition unit 24 displays a first sheet image send screen 144 on the display 14. The first sheet image send screen 144 includes a captured image display section 1441, an imaging conditions display section 1442, an upload button 1443, and a cancel button 1444 that erases the captured image. The image captured by the image capturing unit 16 is displayed in the captured image display section 1441. The sheet affixed to the crack is captured in the image captured by the image capturing unit 16. The captured sheet includes a first layer portion having a first pattern that includes a plurality of line drawings extending in a first direction, and a second layer portion overlapping the first layer portion and having a second pattern that includes a plurality of line drawings extending in a second direction different than the first direction. A moiré that has occurred as a result of the first pattern and the second pattern overlapping is captured in the image, which includes the second layer portion, captured by the image capturing unit 16.

The imaging date when the sheet was imaged, the site location, and other imaging conditions are displayed in the imaging conditions display section 1442. Additionally, along with the imaging conditions of the sheet image, a site ID and a sheet ID sent from the first server 2 are displayed in the imaging conditions display section 1442. When the upload button 1443 is pressed, the sheet image acquisition unit 24 sends signals indicating the sheet image and the measurement date to the first server 2 (S110).

Upon sending of the sheet image and the measurement date from the terminal device 1, the measurement information recording unit 43 of the first server 2 records measurement information including the sent sheet image, measurement date, and the like (S111). Next, the measurement cycle determination unit 44 of the first server 2 determines a measurement cycle at which to measure the crack width of the crack on which the sheet is affixed (S112). Then, the measurement cycle output unit 46 sends a signal indicating the determined measurement cycle to the terminal device 1 (S113). The measurement date display unit 25 of the terminal device 1 calculates the next measurement date of the crack width of the crack on which the sheet is affixed on the basis of the sent measurement cycle, and displays the next calculated measurement date on the display 14 (S114).

Figure 12:
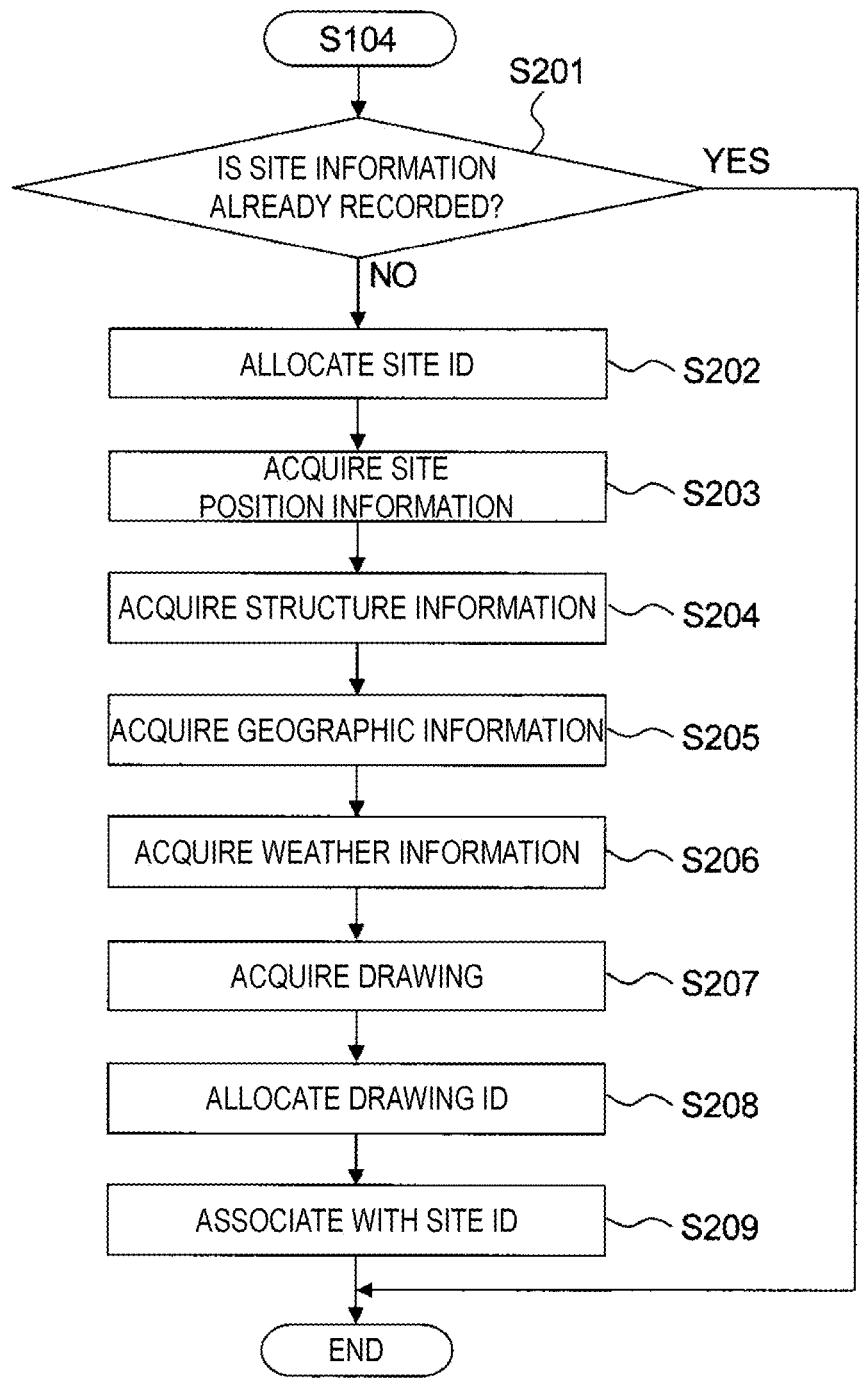
FIG. 12 is a flowchart illustrating a more detailed example of the processing of S104 depicted in FIG. 6.

FIG. 12 is a more detailed flowchart of the processing of S104.

First, on the basis of the site information sent from the terminal device 1, the site information recording unit 41 determines whether or not site information is already recorded (S201). When a flag is included indicating that the site information sent from the terminal device 1 was selected from the existing structure selection section 1411 of the first site information acquisition screen 141 of FIG. 8, the site information recording unit 41 determines that the site information is already recorded (S201—YES) and the processing is ended.

When a flag is included indicating that the new structure selection section 1412 of the first site information acquisition screen 141 of FIG. 8 was pressed and the site information sent from the terminal device 1 was newly inputted in the second site information acquisition screen 142, the site information recording unit 41 determines that the site information is not already recorded (S201—NO) and a new site ID is allocated (S202). Next, the site information recording unit 41 acquires position information including the site information sent from the terminal device 1 as site position information indicating the location of the structure (S203). In one example, latitude and longitude are displayed as the site position information.

Next, the site information recording unit 41 accesses the structure information database 3-1 and acquires the structure information of the structure corresponding to the site information (S204). Next, the site information recording unit 41 accesses the geographic information database 3-2 and acquires the geographic information of the site where the structure is located corresponding to the site information (S205). Next, the site information recording unit 41 accesses the weather information database 3-3 and acquires the weather information of the site where the structure is located corresponding to the site information (S206).

Next, the site information recording unit 41 acquires the structure drawing image 1421 included in the site information sent from the terminal device 1 as the drawing image of the structure (S207). Next, the site information recording unit 41 allocates a drawing ID to the acquired drawing image (S208). Then, the site information recording unit 41 associates the drawing ID allocated in the processing of S208 with the site ID allocated in the processing of S202 (S209).

FIG. 13 is a drawing illustrating an example of the site information and drawing information recorded in the processing of S104. The site information and the drawing information are stored in the first server memory unit 32.

The site information is a data group having the site ID as a key, and includes the site position information, namely the latitude and longitude; the construction year, type, and material of the structure; the ground strength, record high temperature, record low temperature, record snow accumulation, and highest seismic intensity in the past 10 years at the site where the structure is located; the name of the structure; and the like. The drawing information is a data group having the drawing ID as a key, includes the corresponding site ID, and associates the drawing image corresponding to the drawing ID with the site ID.

Figure 14:
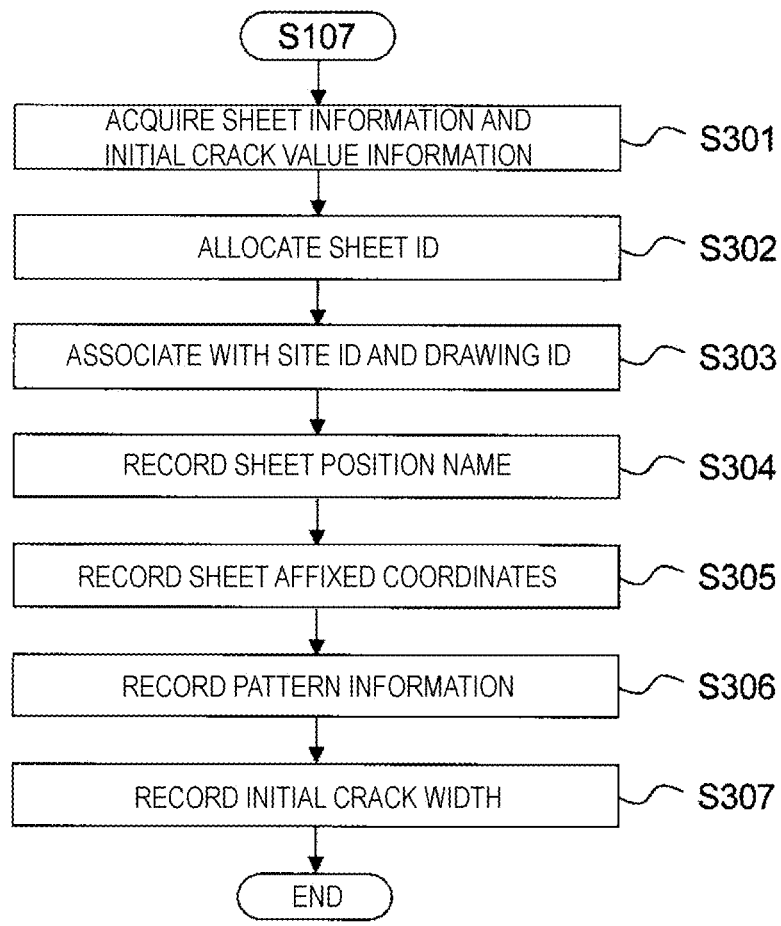
FIG. 14 is a flowchart illustrating a more detailed example of the processing of S107 depicted in FIG. 6.

FIG. 14 is a more detailed flowchart of the processing of S107.

First, the sheet information recording unit 42 acquires the sheet information and the initial crack width sent from the terminal device 1 (S301). Next, the sheet information recording unit 42 issues and allocates a new sheet ID (S302). Then, the sheet information recording unit 42 associates the sheet ID allocated in the processing of S302 with the site ID allocated in the processing of S202 and the drawing ID allocated in the processing of S208 (S303). Next, the sheet information recording unit 42 records the sheet position name included in the sheet information sent from the terminal device 1 (S304), and also records the sheet affixed coordinates included in the sheet information sent from the terminal device 1 (S305). Next, the sheet information recording unit 42 records the pattern information such as the printing pattern, the pitch width, the offset angle, and the like (S306). The sheet part number may also be recorded. Then, the sheet information recording unit 42 records the initial crack width (S307).

FIG. 15 is a drawing illustrating an example of the site information and drawing information recorded in the processing of S104 and also the sheet information recorded in the processing of S107. The sheet information is stored in the first server memory unit 32.

The sheet information is a data group having the sheet ID as a key, and includes the site ID and drawing ID associated with the sheet ID, the sheet position name, the sheet affixed coordinates, the printing pattern, the pitch width, the offset angle, the initial crack width, and the like (and optionally the sheet part number).

Figure 16:
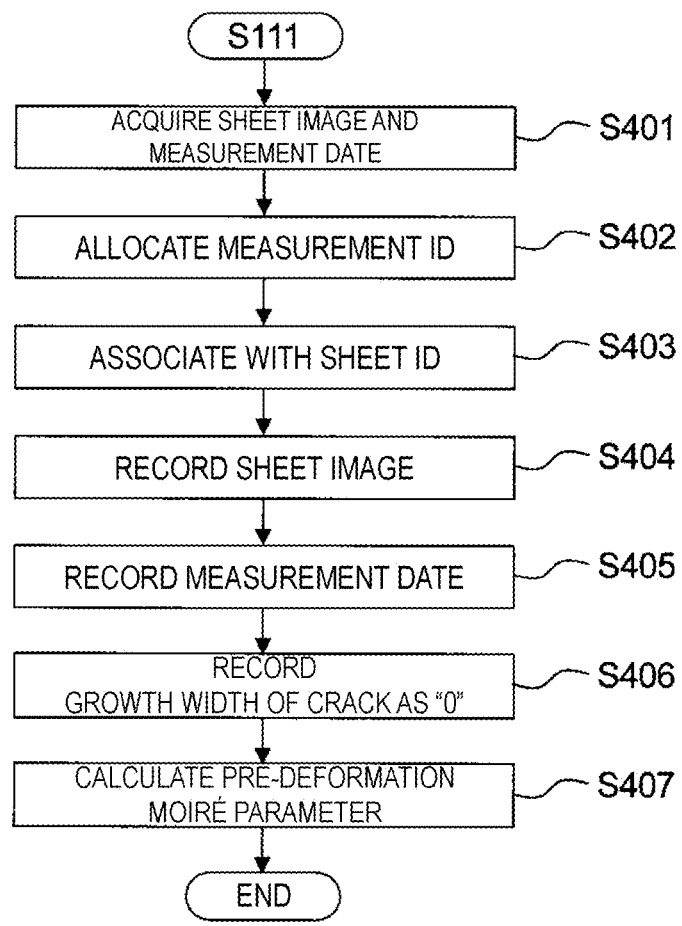
FIG. 16 is a flowchart illustrating a more detailed example of the processing of S111 depicted in FIG. 6.

FIG. 16 is a more detailed flowchart of the processing of S111.

First, the measurement information recording unit 43 acquires the sheet image and the measurement date sent from the terminal device 1 (S401). Next, the measurement information recording unit 43 issues and allocates a new measurement ID (S402). Then, the measurement information recording unit 43 associates the measurement ID allocated in the processing of S402 with the sheet ID allocated in the processing of S303 (S403). Next, the measurement information recording unit 43 records the sheet image sent from the terminal device 1 (S404), and also records the measurement date sent from the terminal device 1 (S405). Next, the measurement information recording unit 43 records "0" for an estimated crack growth width indicating the growth width of the crack (S406). Then, the measurement information recording unit 43 calculates a pre-deformation moiré parameter (S407), and stores the calculated pre-deformation moiré parameter in the first server memory unit 32.

The pre-deformation moiré parameter includes the pitch of the moiré before deformation, namely a first pitch moiré_pitch1, and an inclination angle of the moiré before deformation, namely a first angle of inclination moiré_θ1. The measurement information recording unit 43 acquires spatial frequency information of the sheet image and determines an X-direction component fx and a Y-direction component fy of the spacial frequency of the moiré from the acquired spatial frequency information and the aspect ratio of the sheet image. Then, the measurement information recording unit 43 calculates the first pitch moiré_pitch1 and the first angle of inclination moiré_θ1 from the X-direction component fx and the Y-direction component fy of the spacial frequency of the moiré as follows:

$$\text{moiré\_pitch1} = \sqrt{(fx^2 + fy^2)}$$

$$\text{moiré\_θ1} = \arctan(fy/fx)$$

A detailed explanation of the calculation method of the pre-deformation moiré parameter is described in Japanese Patent Application No. 2015-183136, filed on Sep. 16, 2015.

Figure 17:
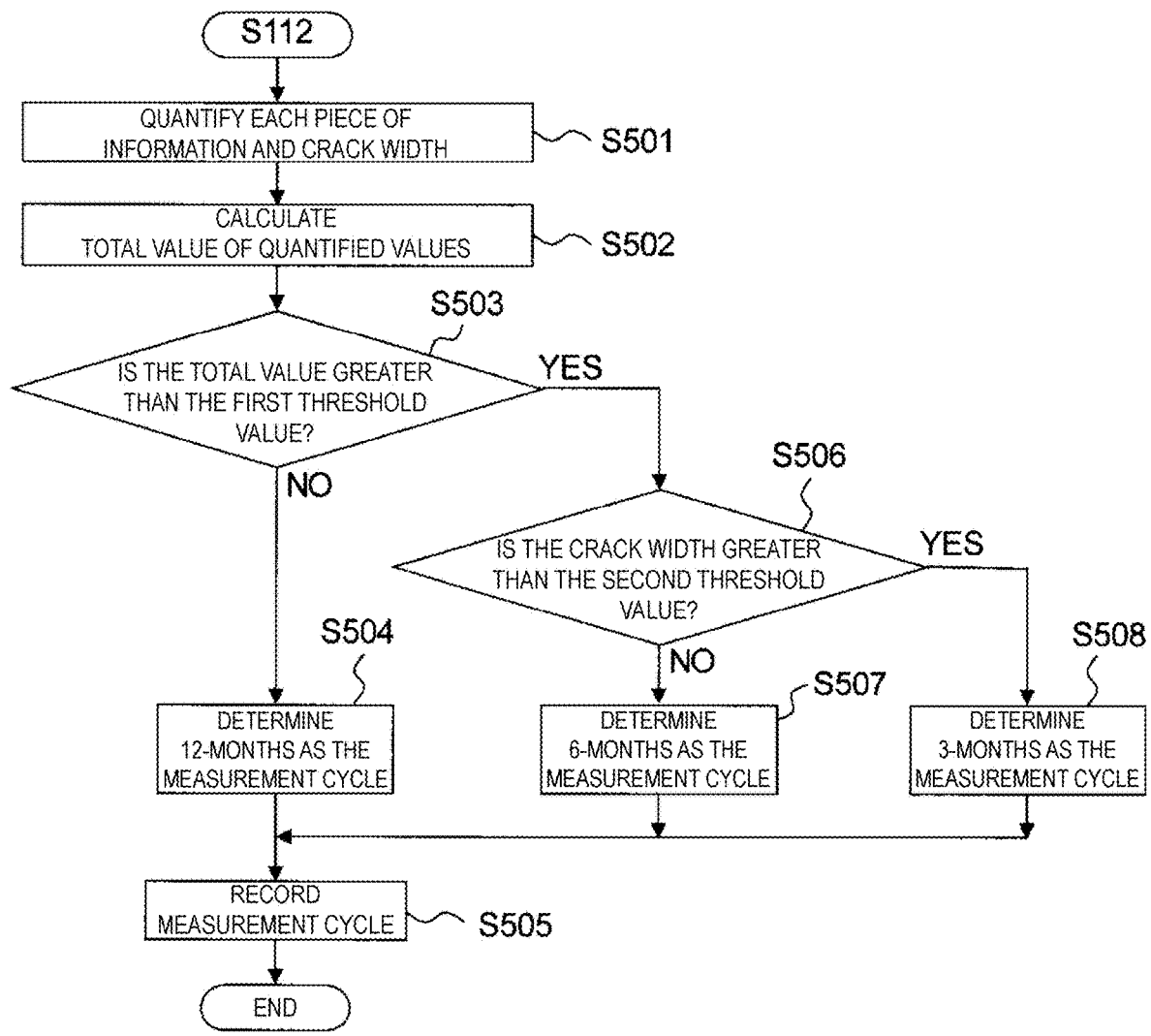
FIG. 17 is a flowchart illustrating a more detailed example of the processing of S112 depicted in FIG. 6.

FIG. 17 is a more detailed flowchart of the processing of S112.

First, the quantification unit 441 quantifies each of the items included in at least one of the geographic information, the weather information, the structure information, and the crack width included in the site information as a numerical value representing a classification (S501), and stores the quantified numerical values in the first server memory unit 32.

FIG. 18 is a drawing illustrating an example of a table containing criteria for quantification processing by the quantification unit 441. The quantification unit 441 executes the quantification processing while referencing this table.

The quantification unit 441 quantifies the geographic information as "1" when the ground where the structure is located is weak, and quantifies the geographic information as "1" when there is salt damage. Additionally, the quantification unit 441 quantifies the geographic information as "1" when an earthquake having a seismic intensity of 4 or greater has occurred in the past 10 years at the site where the structure is located, and quantifies the geographic information as "2" when an earthquake having a seismic intensity of 5 or greater has occurred in the past 10 years at the site where the structure is located. In the same manner, the quantification unit 441 sequentially quantifies the geographic information, the weather information, and the structure information included in the site information. Additionally, the quantification unit 441 quantifies the crack information as "1" when the initial crack width is 1 mm or greater.

Next, the total value calculation unit 442 adds the numerical values quantified by the quantification unit 441 and calculates a total value (S502). Next, the first judgment unit 443 determines whether or not the total value calculated by the total value calculation unit 442 is greater than a first threshold value (S503). When the total value is determined by the first judgment unit 443 to be less than or equal to the first threshold value (S503—NO), the cycle determination unit 445 determines 12-months as the measurement cycle of the crack (S504), and records the 12-month measurement cycle as the measurement cycle of the sheet information (S505). When the total value is determined by the first judgment unit 443 to be greater than the first threshold value (S503—YES), the second judgment unit 444 determines whether or not the initial crack width recorded in the sheet information is greater than a second threshold value (S506). When the initial crack width is determined by the second judgment unit 444 to be less than or equal to the second threshold value (S506—NO), the cycle determination unit 445 determines 6-months as the measurement cycle of the crack (S507), and records the 6-month measurement cycle as the measurement cycle of the sheet information (S505). On the other hand, when the initial crack width is determined by the second judgment unit 444 to be greater than the second threshold value (S506—YES), the cycle determination unit 445 determines 3-months as the measurement cycle of the crack (S508), and records the 3-month measurement cycle as the measurement cycle of the sheet information (S505).

FIG. 19 is a drawing illustrating an example of the site information and the drawing information recorded in the processing of S104, the sheet information recorded in the processing of S107 and S112, and also the measurement information recorded in the processing of S111. The measurement information is stored in the first server memory unit 32.

Figure 20:
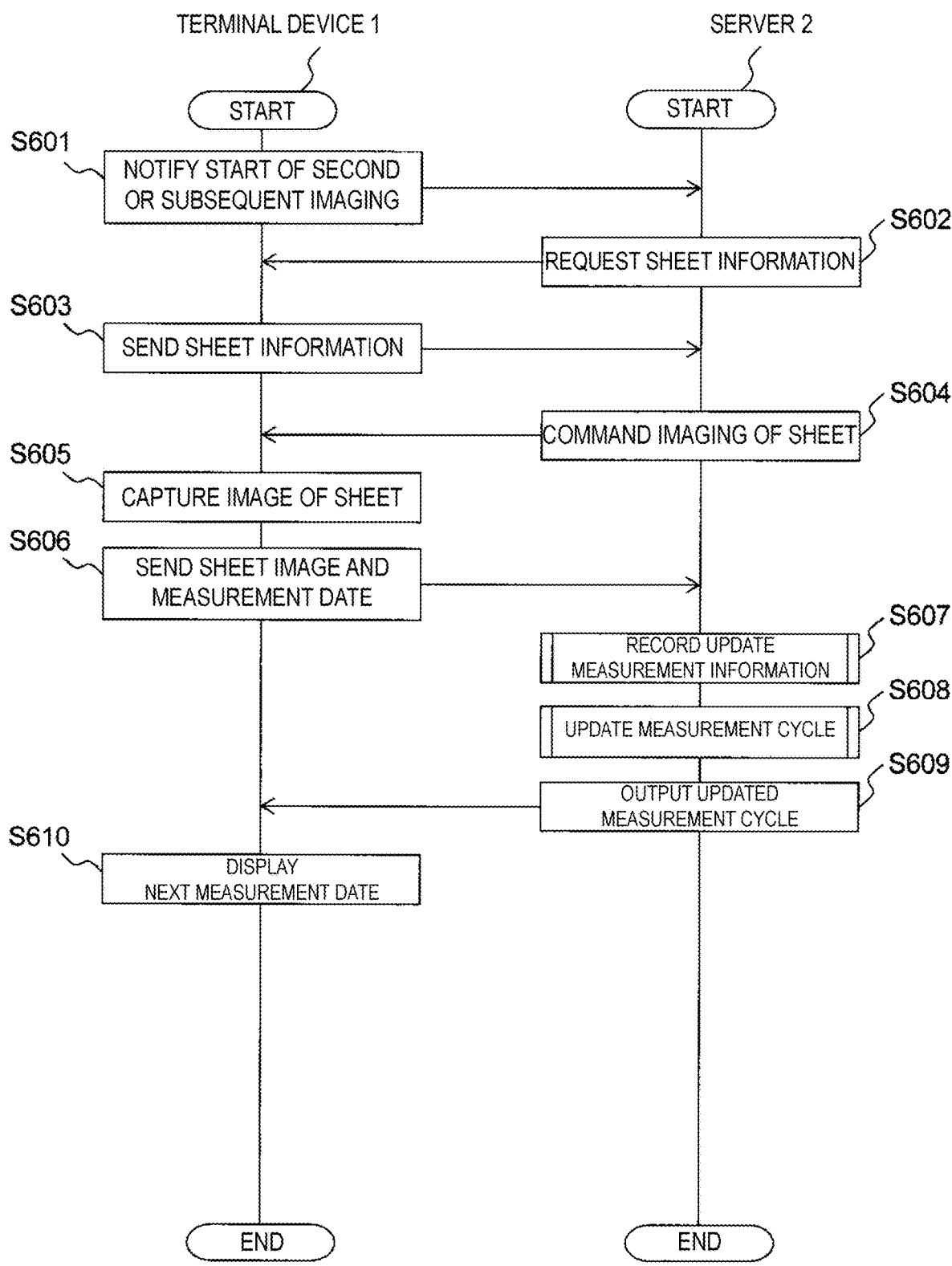
FIG. 20 is a flowchart illustrating an example of measurement cycle update processing at times of second or subsequent imaging by the measurement cycle determination system depicted in FIG. 3.

The measurement cycle determined in the processing of S112 is recorded in the sheet information. The measurement information is a data group having the measurement ID as a key, and includes the sheet ID, the measurement date, the sheet image storage address, the estimated crack growth width, and the like, associated with the measurement ID.
Measurement Cycle Update Processing by the Measurement Cycle Determination System According to the First Embodiment FIG. 20 is a flowchart of measurement cycle update processing by the measurement cycle determination system 100.

First, on the basis of a command of an inspector (not illustrated in the drawings), the terminal device 1 notifies the first server 2 to start second or subsequent imaging of a crack on which the sheet is affixed (S601). More specifically, upon the selection, via the display 14, of an application program for executing crack measurement processing, the measurement start notification unit 21 of the terminal device 1 displays the initial screen 140 depicted in FIG. 7 on the display 14. When an inspector (not illustrated in the drawings) presses a second or subsequent imaging button 1402 of the initial screen 140, the first server 2 is notified to start second or subsequent imaging of the crack on which the sheet is affixed (S601).

Upon being notified to start the second or subsequent imaging of the crack on which the sheet is affixed, the sheet information recording unit 42 of the first server 2 requests the sheet information from the terminal device 1 (S602). Upon receipt of the request for the sheet information, the sheet information acquisition unit 23 of the terminal device 1 acquires the sheet information and sends a signal indicating the acquired sheet information to the first server 2 (S603).

Figure 21:
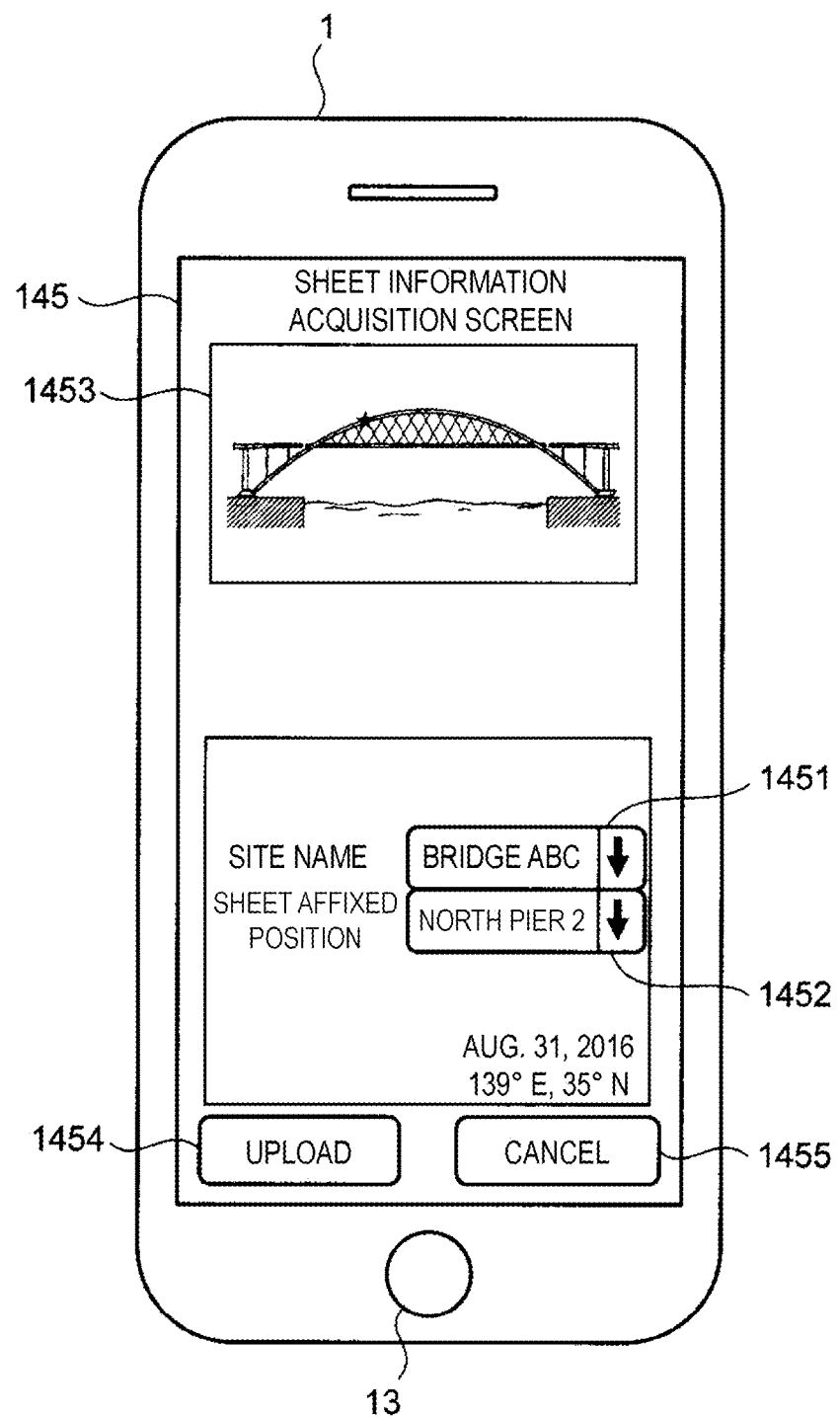
FIG. 21 is drawing illustrating an example of the (second) site information acquisition screen displayed on the terminal device.

FIG. 21 is a drawing illustrating an example of a second sheet information acquisition screen displayed on the display 14 whereby the terminal device 1 that has received the request in S602 acquires the sheet information in S603.

Upon receipt of the request for the sheet information, the sheet information acquisition unit 23 displays a second sheet information acquisition screen 145 on the display 14. The second sheet information acquisition screen 145 includes a site name selection section 1451, a sheet affixed position selection section 1452, a sheet affixed position display section 1453, an upload button 1454, and a cancel button 1455 that erases inputted information. When the site name selection section 1451 is pressed, names of sites are displayed in drop down list format and in a selectable manner. When, for example, "bridge ABC" is selected in the site name selection section 1451, the sheet information acquisition unit 23 accesses the first server memory unit 32 and acquires the site information of "bridge ABC", and the drawing image, drawing information, and sheet information associated with the site information of the "bridge ABC." When the sheet affixed position selection section 1452 is pressed, the sheet information acquisition unit 23 displays affixed positions of sheets in drop down list format and in a selectable manner on the display 14. Upon selection of a sheet affixed position, which is displayed in the sheet affixed position selection section 1452 in drop down format, the selected sheet affixed position is superimposed on the drawing image and the sheet information acquisition unit 23 displays in the sheet affixed position display section 1453. When the upload button 1436 is pressed, the sheet information acquisition unit 23 sends a signal indicating the sheet information that includes the site name selected in the site name selection section 1451 and the sheet affixed position selected in the sheet affixed position selection section 1452 to the first server 2 (S603).

Upon sending of the sheet information from the terminal device 1, the sheet information recording unit 42 of the first server 2 requests the sheet image from the terminal device 1 (S604). Upon receipt of the request for the sheet image, the sheet image acquisition unit 24 of the terminal device 1 captures an image of the sheet affixed to the crack (S605), and sends signals indicating the captured sheet image and the measurement date to the first server 2 (S606).

Figure 22:
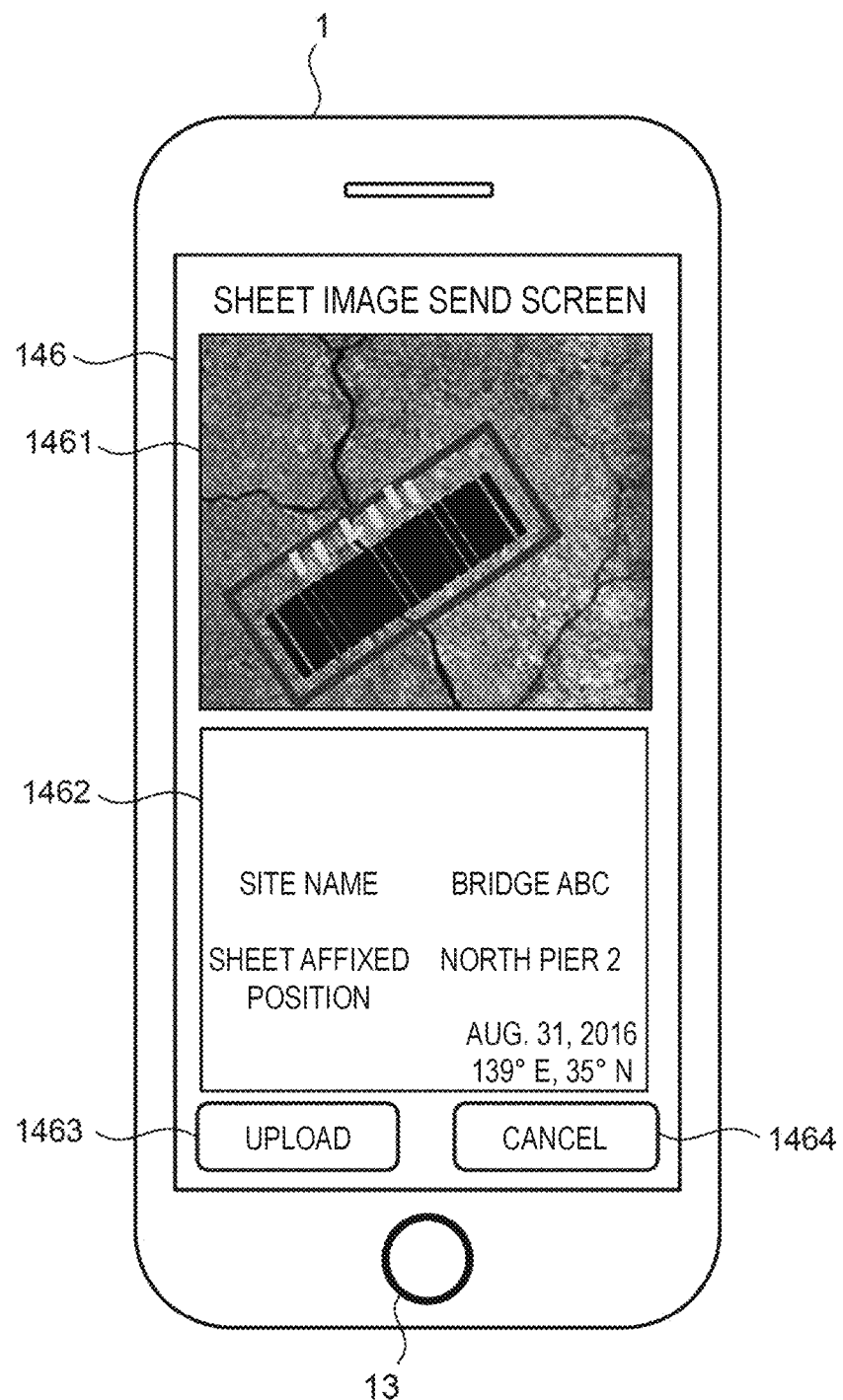
FIG. 22 is drawing illustrating an example of the (first) sheet image send screen displayed on the terminal device.

FIG. 22 is a drawing illustrating an example of a second sheet image send screen displayed on the display 14 whereby the terminal device 1 that has received the request in S604 sends a sheet image acquired at the time of the second or subsequent imaging in S606.

Upon completion of the capturing of the sheet image, the sheet image acquisition unit 24 displays a second sheet image send screen 146 on the display 14. The second sheet image send screen 146 includes a captured image display section 1461, an imaging conditions display section 1462, an upload button 1463, and a cancel button 1464 that erases the captured image. The image captured by the image capturing unit 16 is displayed in the captured image display section 1461. Imaging conditions such as the site name, sheet affixed position, sheet position, and the like are displayed in the imaging conditions display section 1462. When the upload button 1463 is pressed, the sheet image acquisition unit 24 sends signals indicating the sheet image and the measurement date to the first server 2 (S606).

Upon sending of the sheet image and the measurement date sent from the terminal device 1, the measurement cycle updating unit 45 of the first server 2 records update measurement information including the sent sheet image, measurement date, and the like (S607). Next, the measurement cycle updating unit 45 of the first server 2 updates the measurement cycle at which to measure the crack width of the crack on which the sheet is affixed (S608). Then, the measurement cycle output unit 46 sends a signal indicating the updated measurement cycle to the terminal device 1 (S609). The measurement date display unit 25 of the terminal device 1 calculates the next measurement date of the crack width of the crack on which the sheet is affixed on the basis of the sent measurement cycle, and displays the next calculated measurement date on the display 14 (S610).

Figure 23:
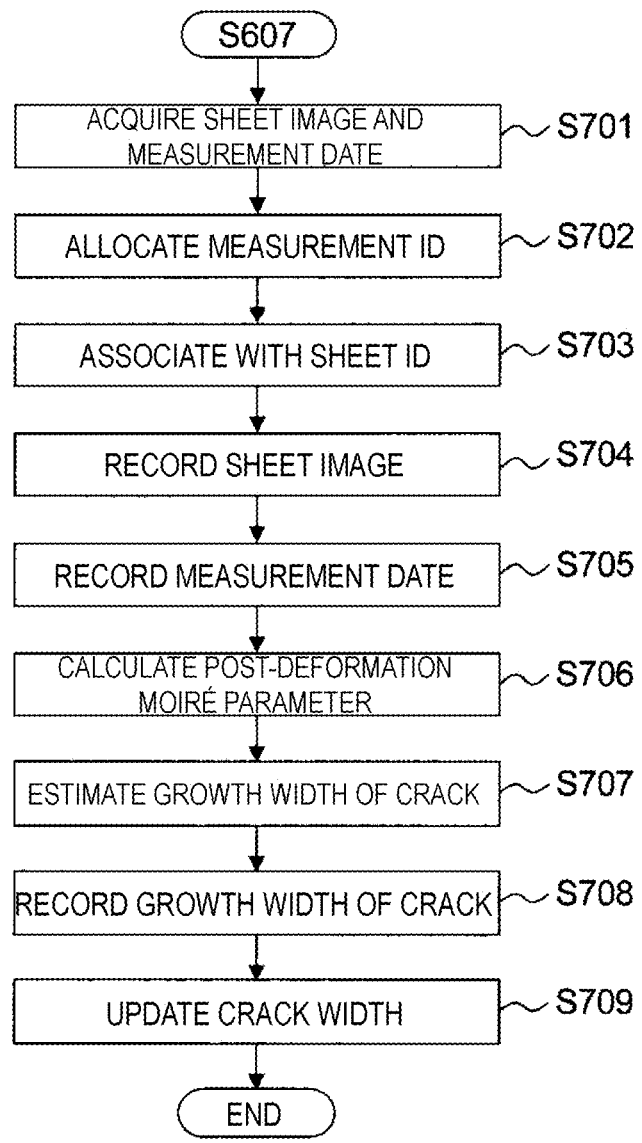
FIG. 23 is a flowchart illustrating a more detailed example of the processing of S607 depicted in FIG. 20.

FIG. 23 is a more detailed flowchart of the processing of S607.

First, the update information recording unit 451 acquires the sheet image and the measurement date sent from the terminal device 1 (S701). Next, the update information recording unit 451 issues and allocates a new measurement ID (S702). Then, the update information recording unit 451 associates the measurement ID allocated in the processing of S702 with the sheet ID allocated in the processing of S303 (S703). Next, the update information recording unit 451 records the sheet image sent from the terminal device 1 (S704), and also records the measurement date sent from the terminal device 1 (S705). Then, the update information recording unit 451 calculates a post-deformation moiré parameter (S706), and stores the calculated post-deformation moiré parameter in the first server memory unit 32.

The post-deformation moiré parameter includes the pitch of the moiré after deformation, namely a second pitch moiré_pitch2, and the inclination angle of the moiré after deformation, namely a second angle of inclination moiré_θ2. The methods for calculating the second pitch moiré_pitch2 and the inclination angle of the moiré after deformation, namely the second angle of inclination moiré_θ2 are the same as the methods for calculating the first pitch moiré_pitch 1 and the first angle of inclination moiré_θ1. As such, detailed description thereof is omitted.

Next, the crack growth width estimation unit 452 calculates the amount of change in the pitch of the first pattern 121 from before to after deformation from the pre-deformation moiré parameter and the post-deformation moiré parameter, and estimates the crack growth width from the calculated amount of change of the pitch (S707).

Figure 24:
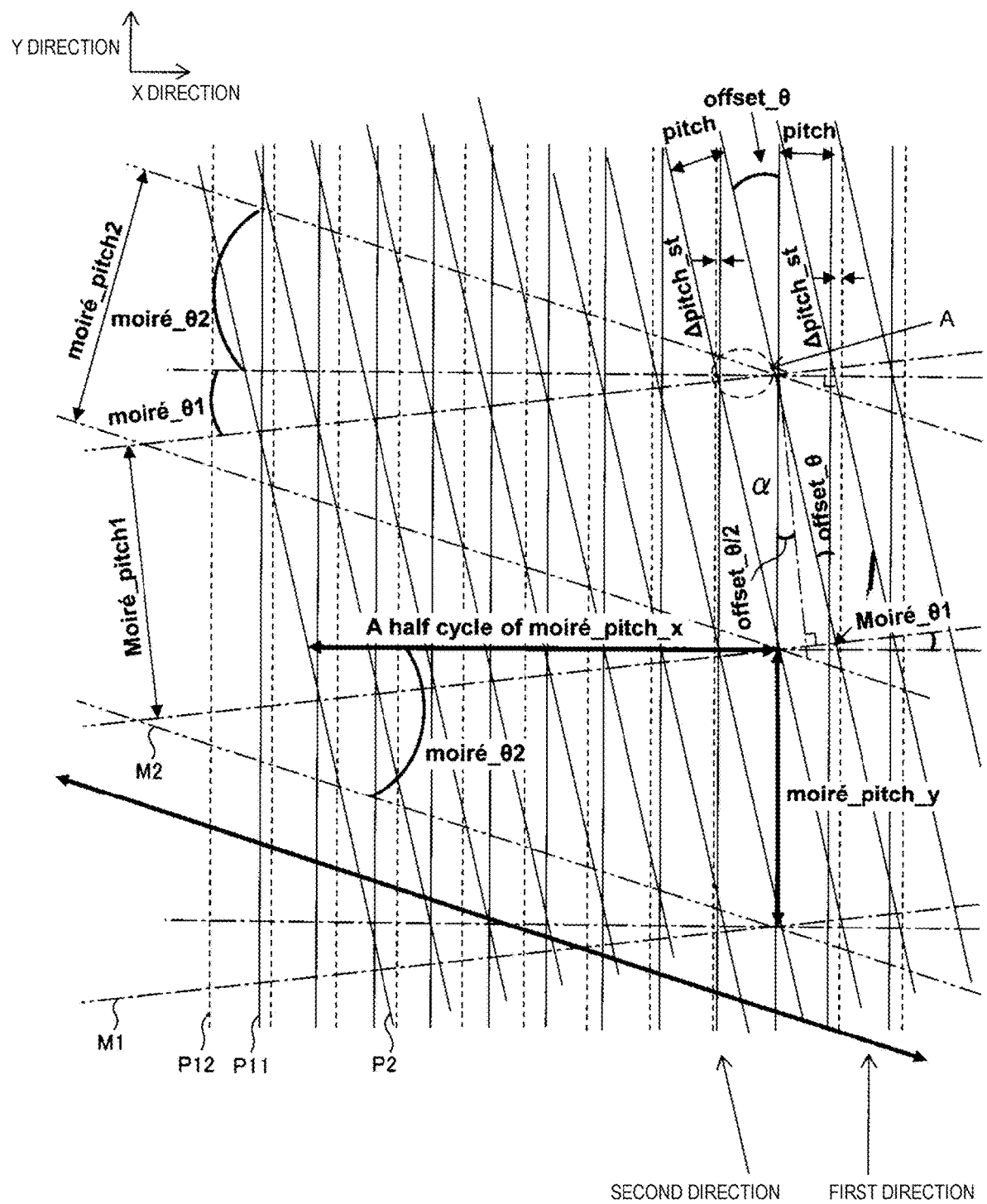
FIG. 24 is a first diagram for explaining the processing of S707 depicted in FIG. 20.

FIG. 24 is a first diagram for explaining the processing of S707. An interval between a plurality of parallel straight lines P11 (depicted as solid lines) extending in a first direction represents the pre-deformation pitch of the first pattern 121, "pitch"; and an interval between a plurality of parallel straight lines P12 (depicted as dashed lines) extending in the first direction represents the post-deformation pitch of the first pattern 121, "pitch+Δpitch_st." Additionally, an interval between a plurality of parallel straight lines P2 (depicted as solid lines) extending in a second direction represents the pitch of the second pattern 122, "pitch." The pitch of the second pattern is the same as the pitch of the first pattern 121. Additionally, an interval between a plurality of parallel straight lines M1 (depicted as dot-dash lines) represents the first pitch moiré_pitch1 of the pre-deformation moiré, and an interval between a plurality of parallel straight lines M2 (depicted as dot-dot-dash lines) represents the second pitch moiré_pitch2 of the post-deformation moiré. The X-direction component of the second pitch moiré_pitch2 is represented as moiré_pitch_x, and the Y-direction component of the second pitch moiré_pitch2 is represented as moiré_pitch_y. The sheet 101 deforms in the X direction, that is, the direction orthogonal to the first direction. Accordingly, the Y-direction component of the pitch of the moiré does not change from before to after deformation of the sheet 101, and is constant at the moiré_pitch_y.

The Y-direction component moiré_pitch_y, indicated as "α" in FIG. 24, of the second pitch of the moiré is expressed from the first pitch moiré_pitch1 of the pre-deformation moiré and the offset angle offset_θ by:

$$\text{moire\_pitch\_}y = \alpha = \frac{\text{moire\_pitch\_init}}{\cos((\text{offset})\_\theta/2)} \quad \text{[Equation 1]}$$

Figure 25A:
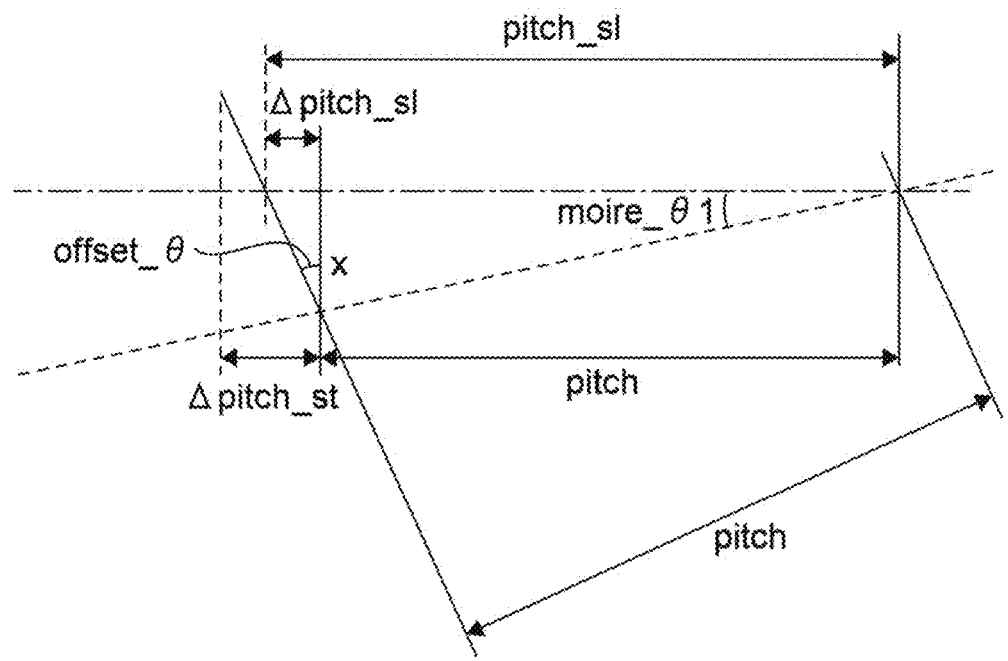
FIG. 25A is a second diagram for explaining the processing of S707.
Figure 25B:
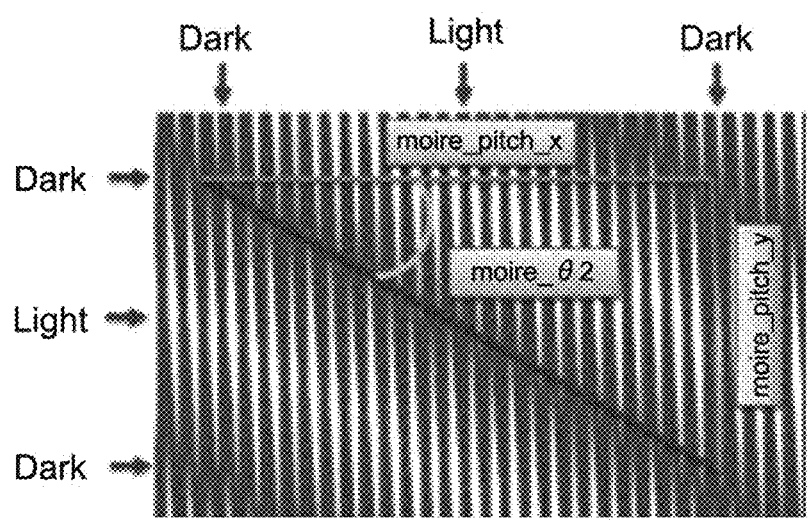
FIG. 25B is a third diagram for explaining the processing of S707.

FIG. 25A is a second diagram for explaining the processing of S707. FIG. 25B is a third diagram for explaining the processing of S707. FIG. 25A is a partially exploded view of a portion of FIG. 24 surrounded by the dashed line indicated by the arrow A. In FIG. 25A, offset_θ represents the offset angle, pitch represents the pitch of the pre-deformation first pattern 121 and the pitch of the pre-deformation second pattern 122, Δpitch_st represents the amount of change of the pitch of the first pattern 121 from before to after deformation, and moiré_θ1 represents the first angle of inclination. Additionally, an inclination pitch pitch_sl and a difference inclination pitch Δpitch_sl are variables that are used in calculations. The inclination pitch pitch_sl is defined by the pitch and the first angle of inclination moiré_θ1 of the second pattern 122, and the difference inclination pitch Δpitch_sl is a difference between the inclination pitch pitch_sl and the pitch of the second pattern 122.

The offset angle offset_θ is expressed from the difference inclination pitch pitch_sl and a length represented as x in FIG. 25A by:

$$\tan(\text{offset}\_\theta) = \frac{\Delta\text{pitch\_sl}}{x} \quad \text{[Equation 2]}$$

Additionally, the first angle of inclination moiré_θ1 is expressed from the pitch of the pre-deformation first pattern 121 and the length represented as x in FIG. 25A by:

$$\tan(\text{moire}\_\theta1) = \frac{x}{\text{pitch}} \quad \text{[Equation 3]}$$

The difference inclination pitch Δpitch_sl is expressed by expanding these two equations by:

$$\Delta\text{pitch\_}sl = \text{pitch}\cdot\tan(\text{offset}\_\theta)\cdot\tan(\text{moiré}\_\theta1) \quad \text{[Equation 4]}$$

On the other hand, the inclination pitch pitch_sl is expressed from the pitch of the pre-deformation first pattern 121 and the difference inclination pitch Δpitch_sl by:

$$\text{pitch\_}sl = \text{pitch} + \Delta\text{pitch\_}sl \quad \text{[Equation 5]}$$

Additionally, the amount of change Δpitch_st of the pitch of the first pattern 121 from before to after deformation, the inclination pitch pitch_sl, and the difference inclination pitch Δpitch_sl are expressed by:

$$n \cdot (\Delta\text{pitch\_st} - \Delta\text{pitch\_sl}) = \frac{\text{pitch\_sl}}{2} \quad \text{[Equation 6]}$$

Here, "n" is a multiple showing how many times the inclination pitch pitch_sl a half cycle of the X component moiré_pitch_x of the second pitch of the post-deformation moiré is equal to. From the equations described above, the multiple n is expressed by:

$$n = \frac{\text{pitch\_sl}}{2 \cdot (\Delta\text{pitch} - \Delta\text{pitch\_sl})} \quad \text{[Equation 7]}$$

On the other hand, the X component moiré_pitch_x of the second pitch of the post-deformation moiré, the inclination pitch pitch_sl, and the multiple n are expressed by:

$$\text{moiré\_pitch\_}x = 2\cdot n\cdot\text{pitch\_}sl \quad \text{[Equation 8]}$$

From these relationships, the X component moiré_pitch_x of the second pitch of the post-deformation moiré can be expressed by:

$$\text{moire\_pitch\_}x = \frac{\text{pitch\_sl}^2}{\Delta\text{pitch\_st} - \Delta\text{pitch\_sl}} \quad \text{[Equation 9]}$$

Additionally, as illustrated in FIG. 25B, the X component moiré_pitch_x of the second pitch of the post-deformation moiré, the Y component moiré pitch_y of the second pitch of the post-deformation moiré, and the second angle of inclination moiré_θ2 can be expressed by:

$$\tan(\text{moire\_}\theta2) = \frac{\text{moire\_pitch\_}y}{\text{moire\_pitch\_}x} \quad \text{[Equation 10]}$$

From the equations described above, the amount of change Δpitch_st of the pitch of the first pattern 121 from before to after deformation is expressed by:

$$\Delta\text{pitch\_st} = \frac{\text{pitch\_sl}^2 \cdot \tan(\text{moire\_}\theta2)}{\text{moire\_pitch\_}y} + \Delta\text{pitch\_sl} \quad \text{[Equation 11]}$$

wherein

Δpitch_sl=pitch·tan(offset_θ)·tan(moiré_θ1), and [Equation 12]

pitch_sl=pitch+Δpitch_sl [Equation 13]

The crack growth width estimation unit 452 calculates the amount of change Δpitch_sl of the pitch of the first pattern 121 from before to after deformation using Equation (1).

The crack growth width estimation unit 452 calculates the growth width of the crack by multiplying the amount of change Δpitch_st of the pitch of the first pattern 121 from before to after deformation by the number of straight lines of the first pattern 121 included in the region where the pitch changes. A detailed explanation of the calculation method of the growth width of the crack is described in Japanese Patent Application No. 2015-183136, filed on Sep. 16, 2015.

Then, the update information recording unit 451 records the growth width of the crack estimated in the processing of S707 (S708). Additionally, the update information recording unit 451 updates the crack width recorded in the sheet information on the basis of the growth width of the crack estimated in the processing of S707 (S709).

The processing of S608 that is executed by the cycle update unit 453 of the measurement cycle updating unit 45 is the same as the processing of S112 described while referencing FIG. 17. As such, detailed description thereof is omitted. The cycle update unit 453 may include a quantification unit 441, a total value calculation unit 442, a first judgment unit 443, and a second judgment unit 444, and may execute the processing of S608 in a manner similar to the measurement cycle determination unit 44. Additionally, the cycle update unit 453 may command the measurement cycle determination unit 44 to execute the processing of S608.

FIG. 26 is a drawing illustrating an example of the site information and the drawing information recorded in the processing of S104, the sheet information including the crack width updated in the processing of S607, and the measurement information including the growth width of the crack recorded in the processing of S607. The sheet information and the measurement information are stored in the first server memory unit 32.

In the measurement information, the estimated crack growth width is the value estimated in the processing of S707. Additionally, in the sheet information, the crack width is a value obtained by adding the estimated crack growth width of the measurement information to the initial crack width depicted in FIG. 19. That is, the estimated crack growth width is estimated on the basis of a comparison of a moiré corresponding to previously acquired image data and a moiré corresponding to presently acquired image data.

Instead of only a single sheet, the measurement cycle determination system 100 may execute the measurement cycle determination processing described while referencing FIG. 6 and the measurement cycle update processing described while referencing FIG. 20 on a plurality of sheets. When the measurement cycle determination processing and the measurement cycle update processing is executed on a plurality of sheets, the site information, the drawing information, the sheet information, and the measurement cycle corresponding to each of the plurality of sheets are stored in the first server memory unit 32.

Advantageous Effects of the Measurement Cycle Determination System According to the First Embodiment The measurement cycle determination system (the measurement cycle determination device, program, method, and the like) according to the first embodiment determines the measurement cycle at which to measure the width of a crack in a structure on the basis of at least one of geographic information, weather information, structure information, and crack information and, as such, the measurement cycle of the width of the crack can be changed depending on the condition of the structure.

Additionally, the measurement cycle determination system according to the first embodiment updates the measurement cycle on the basis of crack information such as the growth width of the crack and, as such, the measurement cycle of the width of the crack can be changed in accordance with changes in the condition of the crack.

Additionally, the measurement cycle determination system according to the first embodiment estimates the growth width of the crack on the basis of sheet images in which moirés are captured and, as such, the growth width of the crack can be estimated easily and with excellent accuracy.

Additionally, the measurement cycle determination system according to the first embodiment determines the measurement cycle on the basis of the total value of numerical values obtained by quantifying items included in the geographic information, the weather information, the structure information, and the crack information and, as such, the measurement cycle can be configured in accordance with the environment of the structure and the condition of the crack.

Additionally, the measurement cycle determination system according to the first embodiment determines the measurement cycle while taking the total value of numerical values obtained by quantifying the items and also the width of the crack into consideration and, as such, a more suitable measurement cycle can be configured in accordance with the width of the crack.

Configuration of a Measurement Cycle Determination System According to a Second Embodiment A measurement cycle determination system according to a second embodiment includes the terminal device 1, the second server 7, the structure information database 3-1, the geographic information database 3-2, and the weather information database 3-3.

Figure 27:
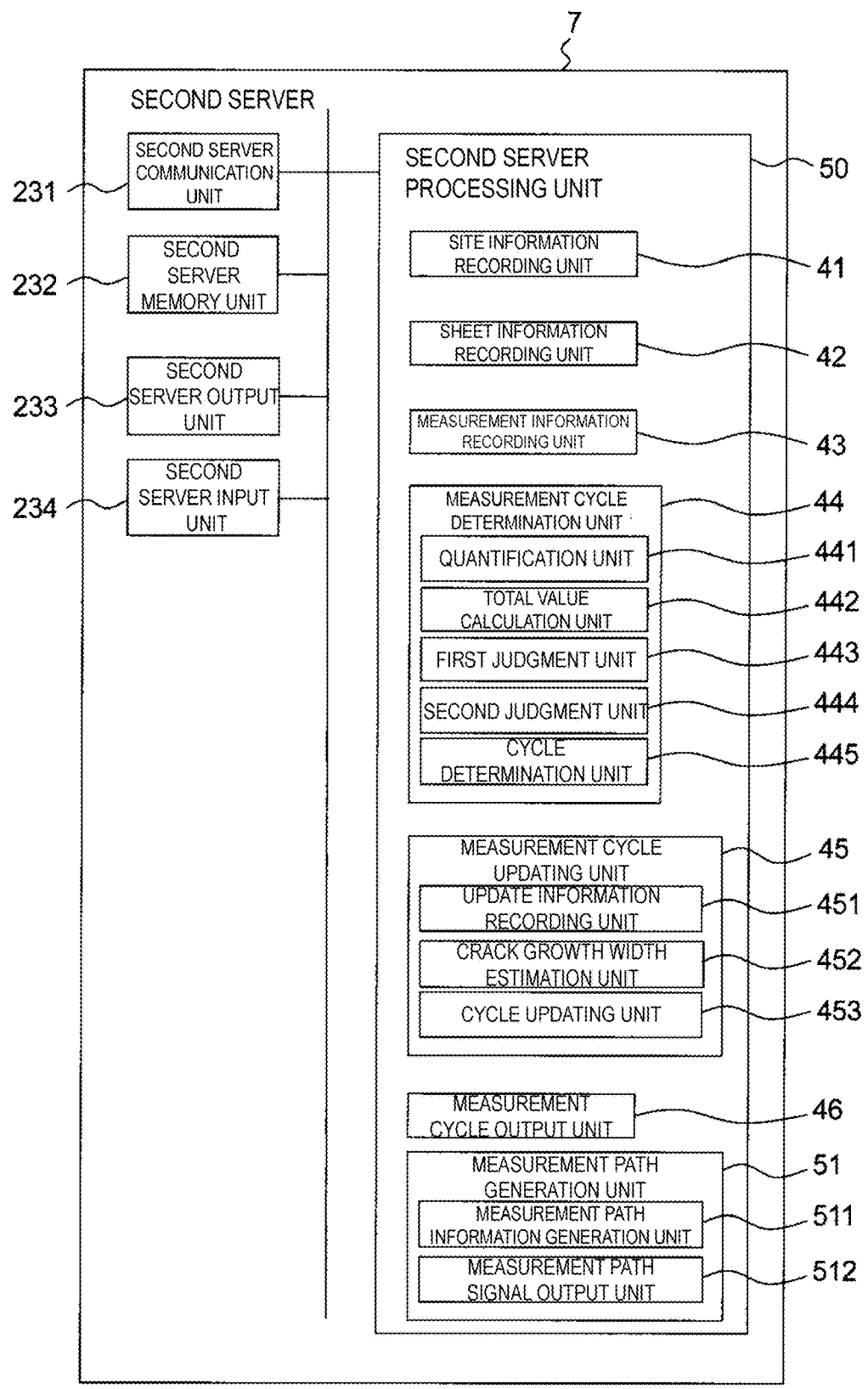
FIG. 27 is a drawing illustrating one example of a schematic configuration of the second server depicted in FIG. 3.

Configuration and Function of the Second Server According to the Second Embodiment FIG. 27 is a drawing illustrating an example of a schematic configuration of an example of the measurement cycle determination device according to the second embodiment, namely the second server 7.

The second server 7 includes a second server communication unit 231, a second server memory unit 232, a second server output unit 233, a second server input unit 234, and a second server processing unit 50. The second server communication unit 231, the second server memory unit 232, the second server output unit 233, and the second server input unit 234 have the same configurations as the first server communication unit 31 to the first server input unit 34, respectively. As such, detailed description thereof is omitted. The second server processing unit 50 differs from the first server processing unit 40 in that it includes a measurement path generation unit 51. The measurement path generation unit 51 includes a measurement path information generation unit 511 and a measurement path signal output unit 512. The second server 7 cooperates with the terminal device 1 in the same manner as the first server 2 to execute the measurement cycle determination processing described while referencing FIG. 6 and the measurement cycle update processing described while referencing FIG. 20. In addition to executing the measurement cycle determination processing and the measurement cycle update processing, the second server 7 also captures images of sheets disposed at a plurality of sites, and executes measurement path generation processing in which measurement path information including a measurement path for when measuring the width of a crack to which the sheet is affixed.

Figure 28:
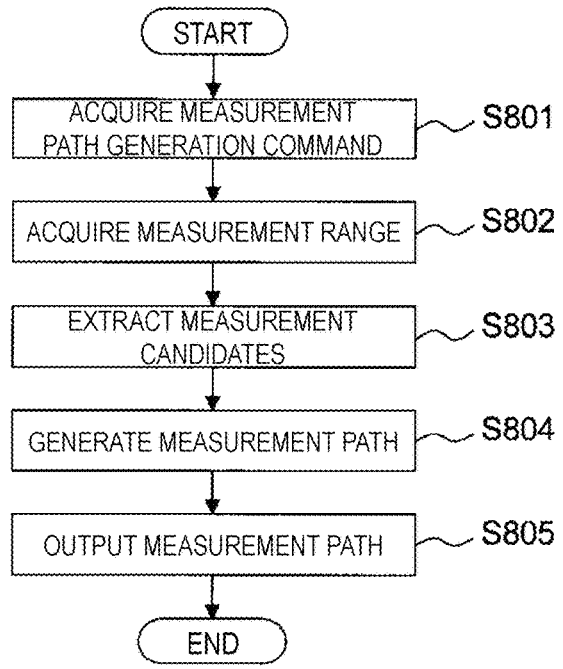
FIG. 28 is a flowchart illustrating an example of measurement path information generation processing by the measurement path generation unit depicted in FIG. 27.

Measurement Path Information Generation Processing by the Measurement Cycle Determination System According to the Second Embodiment FIG. 28 is a flowchart illustrating the measurement path information generation processing by the measurement path generation unit 51.

First, the measurement path information generation unit 511 acquires a measurement path generation command instructing the generation of measurement path information including a path for when measuring the width of a crack by capturing an image of a sheet (S801) and, also, acquires a measurement range indicating a region including the sheet for which the measurement path is to be generated (S802). The measurement path generation command acquired by the measurement path information generation unit 511 includes a scheduled measurement date. The measurement path generation command and the measurement range may be acquired simultaneously, or the measurement path generation command and the measurement range may be acquired sequentially, in this order. Additionally, the measurement path generation command and the measurement range may be acquired from the terminal device 1 or may be acquired via the second server input unit 234.

Next, the measurement path information generation unit 511 extracts a measurement candidate representing the sheet to be imaged for measuring the width of the crack from among the sheets included in the measurement range acquired in the processing of S802 (S803). Specifically, the measurement path information generation unit 511 first extracts the sheets included in the measurement range acquired in the processing of S802. Then, the measurement path information generation unit 511 calculates the next measurement date for each sheet included in the measurement range on the basis of the measurement date included in the latest measurement information of the extracted sheets and the measurement cycle included in the sheet information. Next, the measurement path information generation unit 511 extracts measurement candidates on the basis of the next calculated measurement date. In one example, the measurement path information generation unit 511 extracts sheets, for which the next calculated measurement date is within a predetermined period from the measurement date, as the measurement candidates. In another example, the measurement path information generation unit 511 extracts a predetermined number of sheets, in order of closeness of the next calculated measurement date to the measurement date, as the measurement candidates (S803).

Additionally, the work schedule of a measurer may be taken into consideration. For example, in a case where the next scheduled measurement date of sheets at three locations are recorded in the sheet information as August 3 (sheet AAA), August 16 (sheet AAB), and August 18 (sheet AAC), if the work schedule of the measurer is once per month, and the next work is scheduled for August 1, the measurement path information generation unit 511 extracts all three of the locations as the measurement candidates. Alternatively, if the work schedule of the measurer is twice per month and the next work is scheduled for August 1 and August 15, the measurement path information generation unit 511 extracts sheet AAA as the measurement candidate for August 1 and the sheet AAB and the sheet AAC as the measurement candidates for August 15.

Next, the measurement path information generation unit 511 generates measurement path information including a path for when measuring the width of the cracks by capturing images of the measurement candidates extracted in the processing of S803 (S804). The measurement path information generation unit 511 generates the measurement path information including the path for when measuring the width of the crack of each of the plurality of structures, on the basis of the measurement cycle information stored in the second server memory unit 232 and positional relationship information indicating a positional relationship of each of the plurality of structures. The measurement path information generation unit 511 may generate the path for when measuring the widths of the cracks using publicly known path searching algorithms such as random searching, simulated annealing, or a genetic algorithm.

Figure 29:
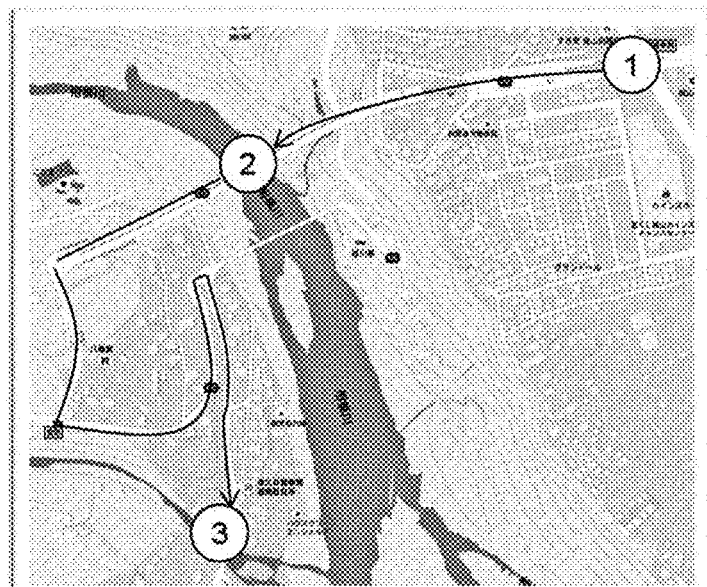
FIG. 29 is a drawing illustrating an example of measurement path information generated in the processing of S805 depicted in FIG. 28.

FIG. 29 is a drawing illustrating an example of the measurement path information generated by the second server 7 in the processing of S805.

Measurement path information 290 includes a map image corresponding to the measurement range, numbers indicating a measurement order of the measurement candidates disposed in the map image, and paths between each of the measurement candidates disposed in the map image. In the measurement path information 290, numbers indicating the measurement order are displayed at points indicated by arrows A to C. Measurement order "1" is displayed at the point indicated by arrow A, measurement order "2" is displayed at the point indicated by arrow B, and measurement order "3" is displayed at the point indicated by arrow C. Additionally, a path between the point indicated by arrow A and the point indicated by arrow B, and a path between the point indicated by arrow B and the point indicated by arrow C are illustrated in the measurement path information 290.

Then, the measurement path signal output unit 512 outputs a measurement path signal indicating the measurement path information including the measurement path generated in the processing of S804 to the terminal device 1 (S805).

Advantageous Effects of the Measurement Cycle Determination System According to the Second Embodiment The measurement cycle determination system according to the second embodiment generates the measurement path information including the path for when measuring the width of the crack of each of the plurality of structures, on the basis of the measurement cycle information and the positional relationship information indicating the positional relationship of each of the plurality of structures. As such, suitable paths can be provided to the inspector.

Configuration of a Measurement Cycle Determination System According to a Third Embodiment A measurement cycle determination system according to a third embodiment includes the terminal device 1, a search terminal device 8, a third server 9, the structure information database 3-1, the geographic information database 3-2, and the weather information database 3-3.

Figure 30:
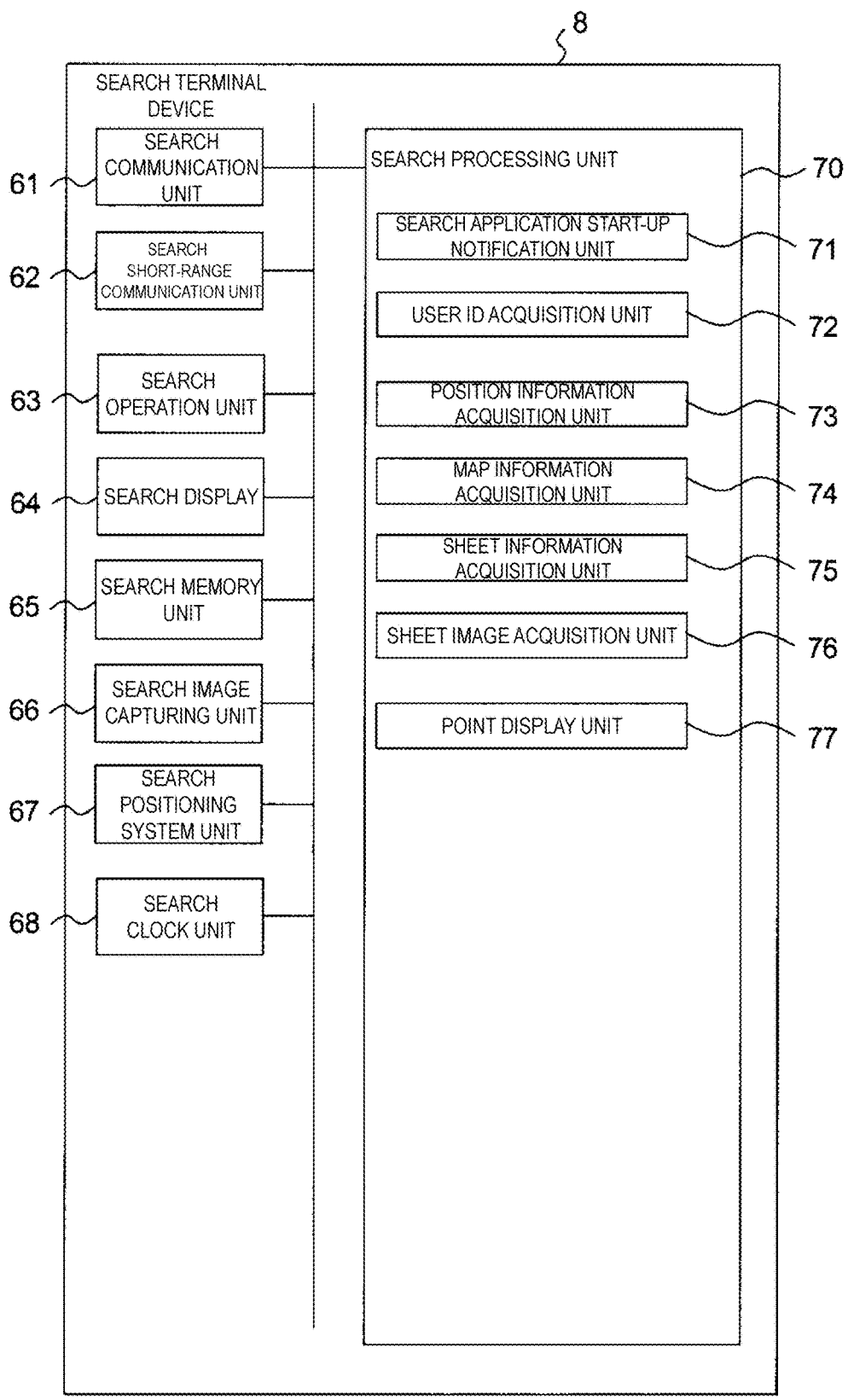
FIG. 30 is a drawing illustrating an example of a schematic configuration of the search terminal device depicted in FIG. 3.

FIG. 30 is a drawing illustrating an example of a schematic configuration of the search terminal device 8.

The search terminal device 8 is, for example, a multifunction mobile phone and includes a search communication unit 61, a search short-range communication unit 62, a search operation unit 63, a search display 64, a search memory unit 65, a search image capturing unit 66, a search positioning system unit 67, a search clock unit 68, and a search processing unit 70. The search communication unit 61 to the search clock unit 68 have the same configurations as the terminal communication unit 11 to the clock unit 18, respectively. As such, detailed description thereof is omitted.

In FIG. 30, a single search terminal device 8 is illustrated, but the measurement cycle determination system according to the embodiments may include a plurality of search terminal devices 8. Additionally, the search terminal device 8 is used by a general user, not by an inspector carrying out maintenance inspection work of a structure such as a bridge, levee, tunnel, or the like. The search terminal device 8 displays a point map on which points are disposed at the positions of sites where sheets are affixed. The points disposed on the point map are values whereby each corresponding crack is weighted. The points corresponding to the sheets are weighted so as to increase the fewer the number of days until the measurement date when the sheet is to be imaged and the width of the crack is to be measured. Additionally, a search application, which displays the total points accumulated when capturing images of the sheets corresponding to the points disposed on the displayed point map, is installed in the search terminal device 8. The user using the search terminal device 8 can get the points displayed on the point map by capturing images of the sheets corresponding to the points and sending image data representing the images including the captured sheets to the third server 9. In one example, the points accumulated by the user can be exchanged for discount coupons for shopping at a predetermined supermarket, for discount coupons for use fees at a predetermined leisure facility, or the like.

The search processing unit 70 is provided with one or a plurality of processors and peripheral circuits thereof. The search processing unit 70 integrally controls the overall operations of the search terminal device 8 and, for example, is a central processing unit (CPU). The search processing unit 70 controls the operations of the search communication unit 61, the search short-range communication unit 62, and the like so that the various processes of the search terminal device 8 are executed with appropriate procedures corresponding to the programs stored in the search memory unit 65, the operations of the search operation unit 63, and the like. The search processing unit 70 executes processing on the basis of the programs (the driver programs, the operating system programs, the application programs, and the like) stored in the search memory unit 65. Additionally, the search processing unit 70 can execute a plurality of programs (the application programs and the like) in parallel.

The search processing unit 70 includes a search application start-up notification unit 71, a position information acquisition unit 72, a position information acquisition unit 73, a map information acquisition unit 74, a sheet information acquisition unit 75, a sheet image acquisition unit 76, and a point display unit 77. Each of the units of the search processing unit 70 is a functional module that is implemented by a program executed on the processor of the search processing unit 70. Alternatively, each of the components that is provided in the search processing unit 70 may be implemented in the search terminal device 8 as an independent integrated circuit, microprocessor, or firmware.

Figure 31:
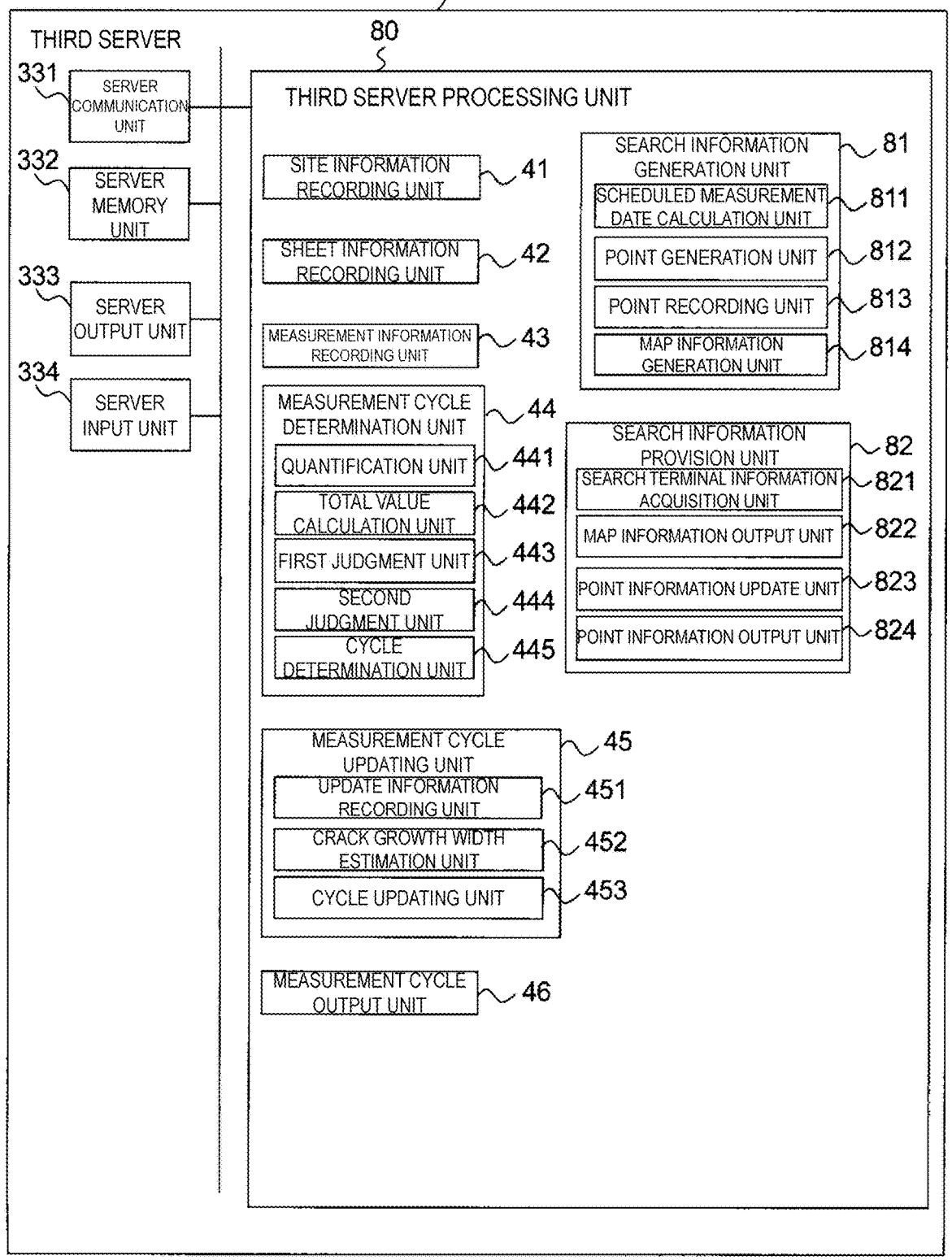
FIG. 31 is a drawing illustrating an example of a schematic configuration of the third server depicted in FIG. 3.

Configuration and Function of the Third Server According to the Third Embodiment FIG. 31 is a drawing illustrating an example of a schematic configuration of an example of the measurement cycle determination device according to the third embodiment, namely the third server 9.

The third server 9 includes a third server communication unit 331, a third server memory unit 332, a third server output unit 333, a third server input unit 334, and a third server processing unit 80. The third server communication unit 331 to the third server input unit 334 have the same configurations as the first server communication unit 31 to the first server input unit 34, respectively. As such, detailed description thereof is omitted. The third server processing unit 80 differs from the first server processing unit 40 in that it includes a search information generation unit 81 and a search information provision unit 82. The search information generation unit 81 includes a scheduled measurement date calculation unit 811, a point generation unit 812, a point recording unit 813, and a map information generation unit 814. The search information provision unit 82 includes a search terminal information acquisition unit 821, a map information output unit 822, a point information update unit 823, and a point information output unit 824. The third server 9 cooperates with the terminal device 1 in the same manner as the first server 2 to execute the measurement cycle determination processing described while referencing FIG. 6 and the measurement cycle update processing described while referencing FIG. 20. The third server 9 executes the measurement cycle determination processing and the measurement cycle update processing and, also, search information generation processing in which search information is generated in which the sheets affixed to the cracks are converted to points, and search information provision processing in which the generated search information is provided.

Figure 32:
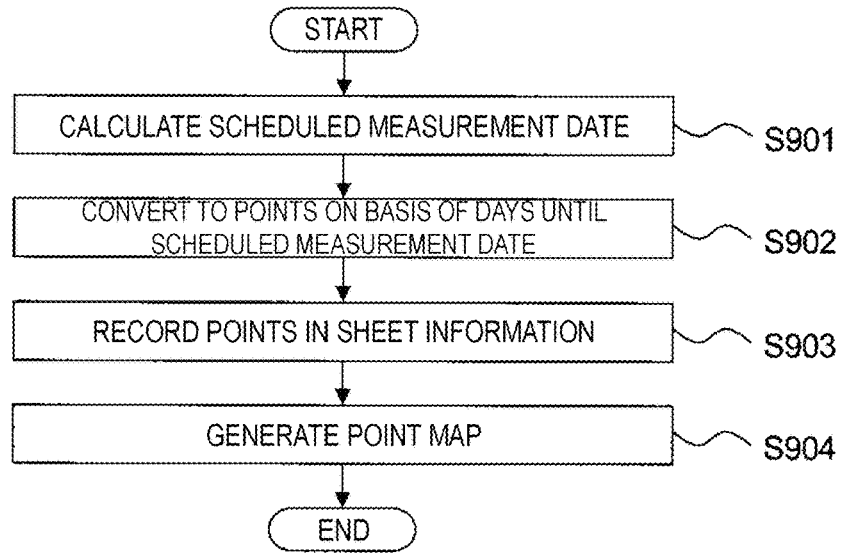
FIG. 32 is a flowchart illustrating an example of search information generation processing by the search information generation unit depicted in FIG. 31.

Search Information Generation Processing by the Measurement Cycle Determination System According to the Third Embodiment FIG. 32 is a flowchart illustrating an example of the search information generation processing by the search information generation unit 81.

First, the scheduled measurement date calculation unit 811 calculates a scheduled measurement date when the crack width is to be measured next from the measurement date recorded in the measurement information and the measurement cycle recorded in the sheet information for each sheet to which a sheet ID is allocated (S901). Next, the point generation unit 812 generates points on the basis of the number of days until the scheduled measurement date when the width of the crack on which the sheet is affixed is to be measured for each of the sheets to which a sheet ID is allocated (S902). For example, the point generation unit 812 may generate 1 point when the number of days until the scheduled measurement date is 1-month, 3 points when the number of days until the scheduled measurement date is 2-weeks, and 5 points when the number of days until the scheduled measurement date is 1-week. Next, the point recording unit 813 records the points generated by the point generation unit 812 in the sheet information (S903). Then, the map information generation unit 814 generates a point map on which the points are displayed by disposing the points recorded in the processing of S903 at positions in a predetermined map image that correspond to the site position information recorded in the site information of each sheet (S904). The point map is an example of search information obtained by converting the sheets affixed to the cracks into points.

Figure 33:
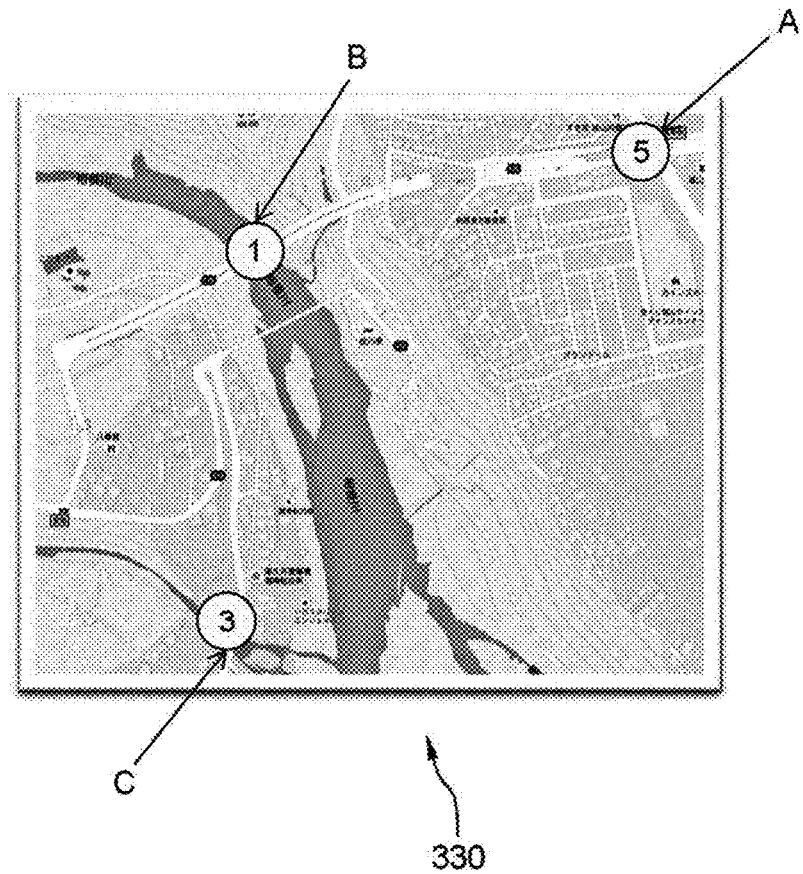
FIG. 33 is a drawing illustrating an example of a point map generated in the processing of S904 depicted in FIG. 32.

FIG. 33 is a drawing illustrating an example of a point map generated by the third server 9 in the processing of S904.

In a point map 330, points are displayed at geographic points indicated by arrows A to C. Point "5" is displayed at the geographic point indicated by arrow A, point "1" is displayed at the geographic point indicated by arrow B, and point "3" is displayed at the geographic point indicated by arrow C.

Figure 34:
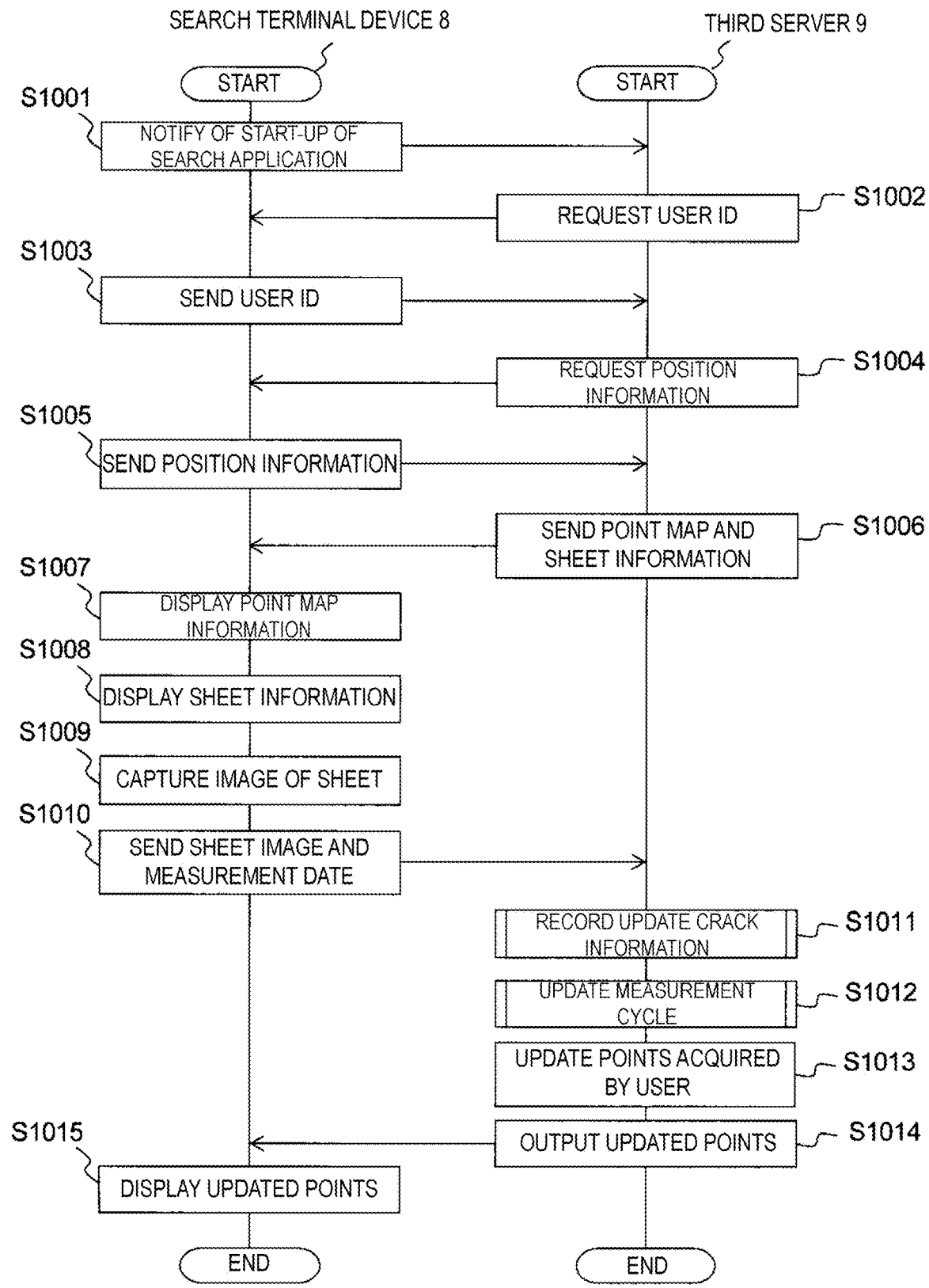
FIG. 34 is a flowchart illustrating another example of search information generation processing by the measurement cycle determination system depicted in FIG. 3.

Measurement Cycle Determination Processing by the Measurement Cycle Determination Device According to the Third Embodiment FIG. 34 is a flowchart of measurement cycle determination processing by the measurement cycle determination system 100.

First the search application start-up notification unit 71 notifies the third server 9 of the start-up of the search application in accordance with the user starting up the search application for searching for sheets corresponding to points (S1001). Upon being notified of the start-up of the search application, the search terminal information acquisition unit 821 requests a user ID from the search terminal device 8 (S1002). Upon receipt of the request for the user ID from the third server 9, the search terminal information acquisition unit 821 acquires the user ID stored in the search memory unit 65 or the like, and sends a signal indicating the acquired user ID to the third server 9 (S1003). Next, the search terminal information acquisition unit 821 stores the sent user ID and also requests position information from the search terminal device 8 (S1004). Next, the position information acquisition unit 73 sends a signal indicating the position information acquired by the positioning system unit 17 to the third server 9 (S1005). Next, the map information output unit 822 selects a point map including the geographic point indicated by the sent position information, and sends the selected point map and the sheet information of the sheets included in the selected point map to the search terminal device 8 (S1006).

Next, the map information acquisition unit 74 displays the point map sent from the third server 9 on the search display 64 (S1007). Next, when a distance, based on the position information acquired by the positioning system unit 17, between any sheet on the point map for which points are shown and the search terminal device is less than or equal to a predetermined threshold, the sheet information acquisition unit 75 displays the sheet information on the search display 64 (S1008). The sheet information displayed on the search display 64 is information indicating the affixed position of the sheet at the site and, in one example, is an image in which the affixed position of the sheet for which points are shown is superimposed on the drawing image and displayed, the same as in the sheet affixed position display section 1453 illustrated in FIG. 21.

Next, the sheet image acquisition unit 76 captures an image of the sheet affixed to the crack on the basis of a command of the user using the search terminal device 8 (S1009), and sends signals indicating the captured sheet image and the measurement date to the third server 9 (S1010).

Upon sending of the sheet image and the measurement date from the search terminal device 8, the measurement cycle updating unit 45 of the third server 9 records update measurement information including the sent sheet image, measurement date, and the like (S1011). Next, the measurement cycle updating unit 45 of the third server 9 updates the measurement cycle at which to measure the crack width of the crack on which the sheet is affixed (S1012). The processing of S1011 and S1012 are the same as the processing of S607 described while referencing FIG. 23 and S112 described while referencing FIG. 18. As such, detailed description thereof is omitted.

Next, the point information update unit 823 adds the points corresponding to the sheet for which the update measurement information was recorded in the processing of S1011 to the number of points associated with the user ID stored in the processing of S1003 and stored, and updates the point information (S1013). Next, the point information output unit 824 sends a signal indicating the point information updated in the processing of S823 to the search terminal device 8 (S1014). Then, the point display unit 77 displays the point information sent in the processing of S1014 on the search display 64 (S1015).

Advantageous Effects of the Measurement Cycle Determination System According to the Third Embodiment The measurement cycle determination system according to the third embodiment weights each of the plurality of cracks on the basis of the measurement cycle information and, thereby, can provide, as a weighting signal, point information in which the plurality of cracks is ordered according to the days until the next measurement date. With the measurement cycle determination system according to the third embodiment, the point information is provided to general users other than inspectors as points that are exchangeable for discount coupons for shopping or the like. As such, general users other than inspectors can be incentivized to measure the widths of the cracks.

Modified Examples of the Measurement Cycle Determination System According to the Embodiments With the measurement cycle determination system according to the first to third embodiments, the measurement information recording unit 43, update information recording unit 451, and the like, which acquire and record the sheet image, function as crack information acquisition units that acquire crack information for cracks that have occurred in structures. However, with the measurement cycle determination system according to the embodiments, the crack information for cracks that have occurred in structures is not limited to sheet images in which moirés occurring in the sheets are captured. For example, a configuration is possible in which a PDA is provided with a function corresponding to the crack growth width estimation unit that estimates the crack growth width from the moiré displayed in the sheet image. In this case, the crack information for a crack that has occurred in a structure may be the estimated crack growth width, or a crack width calculated by adding the estimated crack growth width to the crack width measured at the previous measurement.

Additionally, with the measurement cycle determination system according to the first to third embodiments, the measurement cycle at which the width of the crack is measured is determined on the basis of the geographic information, the weather information, the structure information, and the crack information. However, with the measurement cycle determination system according to the embodiments, a configuration is possible in which the measurement cycle at which the width of the crack is measured is determined on the basis of at least one of the geographic information, the weather information, and the structure information, and also the crack information. Additionally, with the measurement cycle determination system according to the embodiments, a configuration is possible in which the measurement cycle at which the width of the crack is measured is determined on the basis of at least one of the geographic information, the weather information, the structure information, and the crack information.

Additionally, with the measurement cycle determination system according to the first to third embodiments, the determined or updated measurement cycle is output to a PDA as the measurement cycle information. However, a configuration is possible in which the measurement cycle determination system outputs the measurement cycle information related to the determined or updated measurement cycle to a PDA. For example, a configuration is possible in which the measurement cycle information outputted to the PDA is a date when next measuring the width of the crack, or an alert indicating that a date for measuring the width of the crack is closer than a predetermined date threshold value.

Additionally, with the measurement cycle determination system according to the third embodiment, the measurement cycle determination processing was executed using a point map generated in advance by the search information generation unit 81. However, with the measurement cycle determination system according to the embodiments, a point map need not necessarily be used. With the measurement cycle determination system according to the embodiments, a configuration is possible in which the search terminal device superimposes points, according to corresponding position information, on a map that is acquirable via the internet, and displays this map.

Users of the Measurement Cycle Determination System According to the Embodiments It is expected that the measurement cycle determination system will be used by various types of users. For example, use by countries and local governments that are the owners of bridges and tunnels located on national highways and the like, private companies that are the owners of bridges and tunnels located on private railways and the like, and management companies (private and public) that are hired to perform services is contemplated. Additionally, use by owners and management companies when assuming infrastructure such as factories, warehouses, office buildings, and the like is contemplated. Furthermore, use by owners and management companies and also residents and management associations when assuming infrastructure such as residential condominiums, apartment buildings, and the like is contemplated. Moreover, in the third embodiment, use by the general population, incentivized by the users described above, is also contemplated.

The invention claimed is:

1. A measurement cycle determination device comprising:
    a related information acquisition unit configured to acquire at least one of geographic information including items related to a geography of a site where a structure is located, weather information including items related to weather at the site, or structure information indicating one or more of a construction year, a material, or a structure type related to the structure;
    a crack information acquisition unit configured to acquire crack information related to a crack in the structure;
    a measurement cycle determination unit configured to determine, based on the crack information and at least one of the geographic information, the weather information, or the structure information, a measurement cycle at which to measure a width of the crack; and
    a measurement cycle output unit configured to output a measurement cycle signal indicating measurement cycle information related to the determined measurement cycle.

2. The measurement cycle determination device of claim 1, further comprising:
    a measurement cycle updating unit configured to update the measurement cycle based on the crack information, wherein the measurement cycle output unit is configured to output an updated measurement cycle signal indicating the updated measurement cycle.

3. The measurement cycle determination device of claim 2, wherein the crack information includes image data representing a sheet affixed to the crack, the sheet comprising:
    a first layer portion including a first pattern that includes a plurality of line drawings extending in a first direction;
    a second layer portion including a second pattern that overlaps the first layer portion and that includes a plurality of line drawings extending in a second direction different than the first direction; and
    a moiré occurring in the sheet due to first pattern and the second pattern overlapping, and
    wherein the measurement cycle updating unit comprises a crack growth width estimation unit configured to estimate a growth width of the crack based on a comparison of the moiré corresponding to the image data acquired previously and the moiré corresponding to the image acquired presently.

4. The measurement cycle determination device of claim 1, wherein the crack information includes at least one of a growth width of the crack or the width of the crack.

5. The measurement cycle determination device of claim 1, wherein at least one item included in the geographic information, the weather information, the structure information, the crack information is associated with a numerical value, and wherein the measurement cycle determination unit is further configured to determine a predetermined first cycle for the measurement cycle based on a determination that a total value of respective numerical values associated with a predetermined item is less than or equal to a predetermined first threshold value.

6. The measurement cycle determination device of claim 5, wherein the measurement cycle determination unit includes:
    a quantification unit configured to quantify each respective item included in at least one of the geographic information, the weather information, the structure information, and the crack information as a numerical value representing a classification;
    a total value calculation unit configured to calculate the total value by adding the numerical values quantified by the quantification unit; and
    a first judgment unit configured to determine the first cycle for the measurement cycle when the total value is less than or equal to the first threshold value.

7. The measurement cycle determination device of claim 6, wherein the measurement cycle determination unit is further configured to:
    determine a second cycle shorter than the first cycle for the measurement cycle based on a determination that the width of the crack is less than or equal to a second threshold value; and
    determine a third cycle shorter than the second cycle for the measurement cycle based on a determination that the width of the crack is greater than the second threshold value.

8. The measurement cycle determination device of claim 7, wherein:
    the measurement cycle determination unit further includes a second judgment unit configured to;

determine the second cycle for the measurement cycle based on a determination that the total value is greater than the first threshold value and the width of the crack is less than or equal to the second threshold value; and determine the third cycle for the measurement cycle based on a determination that the total value is greater than the first threshold value and the width of the crack is greater than the second threshold value.

9. The measurement cycle determination device of claim 5, wherein the measurement cycle determination unit is further configured to determine a cycle shorter than the first cycle for the measurement cycle based on a determination that the total value is greater than the first threshold value.

10. The measurement cycle determination device of claim 1, wherein the measurement cycle information includes at least one of the measurement cycle, a date associated with a next measurement of the width of the crack, or an alert indicating that a date for measuring the width of the crack is closer than a predetermined date threshold value.

* * * * *